United States Patent [19]
Maslak

[11] Patent Number: 5,591,848
[45] Date of Patent: Jan. 7, 1997

[54] SPIROCONJUGATED CHARGE-TRANSFER DYES FOR OPTICAL APPLICATIONS

[75] Inventor: Przemyslaw B. Maslak, Boalsburg, Pa.

[73] Assignee: The Penn State Research Foundation, University Park, Pa.

[21] Appl. No.: 320,090

[22] Filed: Oct. 7, 1994

[51] Int. Cl.$^6$ .................. C07D 277/64; C07D 235/12; C07D 243/04; C07D 239/70
[52] U.S. Cl. .................. 540/543; 544/231; 544/6; 548/301.1; 548/147; 549/336; 549/17; 549/16; 549/32
[58] Field of Search .................. 544/231; 540/543; 548/301.1

[56] References Cited

PUBLICATIONS

Gleiter, R. et al. *Chem. Ber.* 127, 2215–2224 (1994).

Primary Examiner—Mukund J. Shah
Assistant Examiner—King Lit Wong
Attorney, Agent, or Firm—Thomas J. Monahan

[57] ABSTRACT

New intramolecular charge-transfer organic dyes are described. The design of these molecules is based on the phenomenon of spiroconjugation, and it provides a modular approach to the preparation of unique materials with interesting optical properties. In the dyes of the invention, the lowest unoccupied molecular orbital (LUMO) of the acceptor part (based on indandione) is spiroconjugated with the highest unoccupied molecular orbital (HOMO) of the donor part (amines, alcohols and thiols). The interaction between the donor and acceptor is controlled by the energy and symmetry of the frontier orbitals. The novel dyes described herein, with predictable and tunable optical properties, can be used in many optical applications including nonlinear optics (NLO).

4 Claims, No Drawings

5,591,848

SPIROCONJUGATED CHARGE-TRANSFER DYES FOR OPTICAL APPLICATIONS

BACKGROUND OF THE INVENTION

The present invention relates to the field of organic compounds with optical properties. More specifically it relates to novel dyes with predictable and tunable optical properties, which can be used in many optical applications including nonlinear optics (NLO). The present invention describing novel materials and methods of their preparations may prove especially useful in photonics.

Photonics, the optical analogue of electronics, is a new promising area of technology important in computing or communication. This new field critically depends on preparation of new materials with predictable and tunable optical properties. (Dalton, L. R. *Nature* 1992, 359, 269., Eaton, D. F.; Meredith, G. R.; Miller, J. S. *Adv. Mater.* 1992, 4, 45). Organic materials based on charge-transfer (CT) interactions play an important role in this field. (Prasad, P. N.; Williams, D. J. *Introduction to Nonlinear Optical Effects in Molecules and Polymers*, Wiley-Interscience, New York 1991,. Khanarian, G. Ed.; *Molecular and Optoelectronic Materials: Fundamentals and Applications*, SPIE: San Diego 1986, Eaton, D. F. *Science* 1991, 253, 281, Marder, S. R.; Gorman C. B.; Tiemann, B. C.; Cheng, L.-T. *J. Am. Chem. Soc.* 1993, 115, 3006). Described herein is a new class of organic charge-transfer dyes wherein the acceptor and donor parts are spiroconjugated. (Simmons, H. E.; Fukunaga, T. *J. Am. Chem. Soc.* 1967, 89, 5208, Hoffmann, R. Imamura, A.; Zeiss, G. D. *J. Am. Chem. Soc.* 1967, 89, 5215, Durr, H.; Gleiter, R. *Angew. Chem. Int. Ed. Engl.* 1978, 17, 559) This relatively weak three dimensional conjugation allows for the implementation of a modular design of new materials, i.e. the adjustments within donor and acceptor moieties (tunability) may be made independently and lead to materials with expected properties (predictability).

SUMMARY OF THE INVENTION

In accordance with present invention, a new type of intramolecular charge-transfer dyes are described. The novel class of compounds is constructed from an acceptor part and the donor part which are joined through a spiro link in such a way that the π-systems of the donor and acceptor are perpendicular to each other. The lowest unoccupied molecuar orbital (LUMO) of the acceptor part in these compounds is spiroconjugated with the highest occupied molecular orbital (HOMO) of the donor part. The interaction between the donor and acceptor is controlled by the energy and symmetry of these frontier orbitals. The spiroconjugation allows for modular design of the new dyes, wherein the donor and acceptor parts may be adjusted independently.

The new compounds of the invention have been prepared using condensation reactions between ninhydrin derivatives and aromatic diamines, dialcohols, dithiols, aminoalcohols, aminothiols, and hydroxythiols. These novel compounds are useful in a variety of optical applications including nonlinear optical devices. Another aspect of this invention is a novel approach to design of materials with large difference between the ground state and the excited state dipole moments.

OBJECTS OF THE INVENTION

An object of this invention is to provide novel organic dyes with predictable and tunable optical properties, which can be used in many optical applications including nonlinear optics.

Another object of this invention is to provide a method for preparation of said chemical compounds.

Yet another object of this invention is to provide a novel approach to design of materials with large differences between the ground state and the excited state dipole moments.

These and other objects and advantages of this invention over prior art and a better understanding of its use will become readily apparent from the following description and are particularly delineated in the appended claims.

DETAILED DESCRIPTION OF THE INVENTION

Nonlinear optical processes are conveniently viewed as dielectric phenomena. Polarization of the molecules or materials in intense electric or electromagnetic fields is described by the field-dependent dipole moment expansion:

$$P = P_o + a \cdot E + b \cdot E \cdot E + c \cdot E \cdot E \cdot E + \ldots$$

where P corresponds to the dipole of the molecule (µ) or bulk polarization of the material (P), $P_o$ is the intrinsic dipole moment of the molecule ($\mu_o$) or the material ($P_o$), E is the electromagnetic field vector and a, b and c correspond to polarizabilty ($\alpha$), hyperpolarizability ($\beta$) and second hyperpolarizabilty ($\gamma$) constants of the molecule, or to the first- ($\chi^{(1)}$), second- ($\chi^{(2)}$), and third-order ($\chi^{(3)}$) susceptibility, respectively, of the material.

The second order non-linear effects dependent on $\beta$ or $\chi^{(2)}$ include second-harmonic generation (frequency doubling), frequency mixing and electro-optic effect (voltage-dependent refraction). These effects are symmetry dependent and vanish in centrosymmetric environment. The third order effects related to $\gamma$ or $\chi^{(3)}$ incorporate third-harmonic generation, frequency mixing, phase conjugation (holography), photorefraction, optical bistability and Kerr effect (intensity dependent refraction). They have no symmetry restriction.

Many organic and organometallic materials which are highly polarizable have been shown to exhibit large (but still unsatisfactory for many applications) NLO effects. In general, the macroscopic nonlinear response depends on the magnitude of molecular nonlinearities and on ordering of molecules in the medium. The improvements are possible in both of these areas. However, the state of art in our ability to control the ordering of molecules in bulk materials is still very unrefined. (Desiraju, G. R. *Crystal Engineering*, Elsevier, Amsterdam, 1989). More progress have been made in defining the structural and electronic factors contributing to optical nonlinearity. It has been recognized that for second order effects conjugated donor-acceptor type compounds show special promise. In these compounds, a pronounced charge transfer accompanies the transition from the ground to the excited state. A simplified two-level model developed for such cases indicates that $\beta$ is directly proportional to the dipole moment difference ($\Delta\mu$) between the states and to the square of the transition dipole moment and inversely proportional to the square of the transition energy. No similar model exists for the third order effects but an extended conjugation is believed to be required.

Presented in this disclosure is a new class of optical charge-transfer materials based on spiroconjugation i.e. the ability of two perpendicular π-networks to interact. This approach allows researchers to implement a modular design of new materials wherein the adjustments within the donor and acceptor moieties (tunability) may be made almost independently of each other and lead to materials with better controlled properties (predictability). The optical properties of the prepared materials can be measured, and the photophysical studies can be conducted to understand the electronic origins of the observed effects in order to refine the design. (Maslak, P.; Chopra, A. *J. Am. Chem. Soc.* 1993, 115, 9331, Maslak, P.; *Adv.Mater.* 1994, 6, 405)

The present invention has theoretical and practical implications. It enhances our understanding of the principles of interaction of molecular solids with light. Also, as the results obtained in laboratory investigation indicate, these compounds show promising NLO properties, and may be useful for development of technologically useful materials.

A detailed embodiment of the present invention involving a novel class of compounds is herein disclosed. However it is understood that the preferred embodiment is merely illustrative of the invention which may be embodied in various forms and applications accordingly, specific structural and functional details disclosed herein are not to be interpreted as limiting, but merely as a support for the invention as claimed and as appropriate representation for the teaching one skilled in the art to variously employ the present invention in any appropriate embodiment.

The design of compounds presented in this invention, is based on the phenomenon of spiroconjugation. i.e. the ability of two mutually perpendicular π-networks that are joined by a spiro atom to interact. The general structure of the new compounds is represented by formula I in Scheme 1. The spiro atom (S) is connected to four atoms ($M_1$, $M_2$, $M_3$, $M_4$,) that are a part of a conjugated system or bear lone electron pairs. These atoms are in turn connected through aromatic or conjugated linkers ($L_1$, $L_2$), forming an electron-deficient acceptor part ($A=M_1-L_1-M_2$) and an electron rich donor part ($D=M_3-L_2-M_4$) The four orbitals on atoms direct attached to the spiro atom provide the required overlap between the two sets of π-orbitals. Such overlap leads to formation of molecular orbitals spanning the entire molecule, yielding one bonding and one antibonding combination. The strength of interaction between these orbitals is controlled by symmetry, and it depends on their overlap and on their relative energies (the smaller the energy separation the stronger the interaction).

SCHEME 1

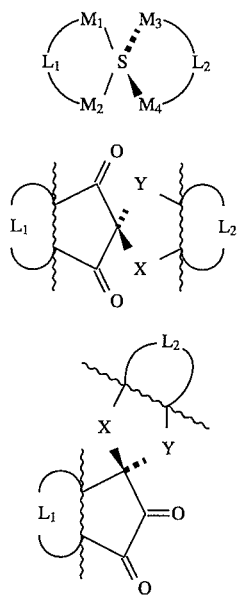

X, Y = O, S, NR (R = alkyl, aryl)

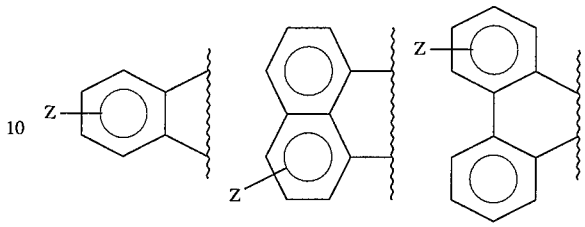

Z = a substituent or substituents chosen from the group containing MeO, RO, $NO_2$, CN, $NH_2$, $NMe_2$, $^+NMe_3$, CN, SMe, OH, $SO_2R$, $OSO_2R$, halogens From the point of view of CT interactions, the highest occupied (HOMO) and the lowest unoccupied (LUMO) orbitals are the most important. It is thus essential for the design of the invention that these frontier orbitals of the donor part (D) and the acceptor part (A) satisfy the symmetry requirement, forming spiroconjugated molecular orbitals. The relatively weak three-dimensional conjugation between selected orbitals of A and D allows for the implementation of a convenient modular design of new materials. Electronic structure adjustments within the A and D moieties may be made almost independently of each other and should lead to materials with better controlled physical properties.

If the LUMO of the acceptor (A) and the HOMO of the donor (D) have the same symmetry, i.e. are antisymmetric vs. the two molecular planes, the interaction between them leads to the lowering of HOMO's energy and to the increase in the LUMO's energy. In addition, both these orbitals mix in a little of each other's character, i.e. the HOMO has some electron density on the acceptor moiety and the LUMO has non-zero p-orbital coefficients on the donor part. The HOMO-LUMO transition is thus allowed in these cases and corresponds, to a full charge transfer between the moieties. (Mulliken, R. S.; Pearson, W. B. *Molecular Complexes: A Lecture and Reprint Volume,* Wiley-Interscience, New York 1969).

If the HOMO of the donor and the LUMO of the acceptor have different symmetries vs. the two molecular planes, the interaction between them is weak, and the HOMO-LUMO (charge-transfer) transition is formally forbiden, leading to low extinction coefficients.

A number of compounds were prepared according to the design principles described above. Their optical properties in solution and in the solid state have been probed.

Compounds of general formula II and III shown in Scheme 1 were constructed from an acceptor part (the substituted indandione moiety) and the donor part (substituted aromatic diamines, dialcohols, dithiols, aminoalcohols, aminothiols and hydroxythiols). The spiro junction allows for a spatial penetration of the lone pair orbitals on the heteroatom (N, O or S) and the p orbitals on carbon atoms of the carbonyl groups or the aromatic residue of the acceptor.

These spiro compounds were prepared by the condensation of ninhydrin with the corresponding donors. All spiro compounds prepared showed the presence of new absorption bands (i.e. bands that are not characteristic of separate acceptor or donor moieties) in the visible region The bands followed the Beer-Lambert law over more than a thousand-fold change in concentrations, indicating the intramolecular nature of the transition.

In derivatives of compounds II and III where the donor group is based on the phenyl substituents, the symmetry of the donor's HOMO is different than the symmetry of the acceptor's LUMO. The interaction between the components is weak, and mainly of inductive nature. As the result, the HOMO-LUMO transition is forbidden. The charge-transfer bands have low extinction coefficients and relatively low energy of transition.

In contrast, the naphthyl or biphenyl based donors have orbitals that are antisymmetric vs. the plane of the acceptor. These orbitals strongly spiroconjugate with the LUMO's of the acceptor parts. The HOMO's energy is significantly lowered by the spiroconjugation and the energy of the LUMO is raised correspondingly, increasing the HOMO-LUMO gap. As the result of this orbital mixing, the CT transition is allowed and significantly shifted to higher energies.

The charge-transfer bands showed pronounced solvatochromic effect. Using the solvatochromic data from several solvents, and following the McRae formlism, (Paley, M. S.; Harris, J. M.; Looser, H.; Baumert, J. C.; Bjorklund, G. C.; Jundt, D.; Twieg, R. J. *J. Org. Chem.* 1989, 54, 3774. (c) McRae, E. G. *J. Phys. Chem.* 1957, 61,562.) the excited state dipole moments of these compounds can be estimated to be ca. 9–17 debyes for most of the compounds in the direction opposite to the ground state dipoles. These estimates are consistent with the HOMO-LUMO interactions described above. The ground state have dipoles varying from 2 to 9 debyes, with the dicarbonyl moiety being the electron-deficient end. The excited state resembles an indandione radical anion-donor radical cation pair. Thus the net change of the dipole moment accompanying the transition from the ground to the excited states is large (up to 25 debyes), and according to the two-state model these compounds can have large hyperpolarizabilities.

Preliminary results indicate that the excited states of compounds II and III are non-fluorescent. Most importantly, solutions of these compounds produce intense visible light in the EFISH experiments when irradiated with the 1064 nm laser light.

There are several important features which make these CT compounds of special interest. The strength of CT interactions can be easily manipulated by the adjustment of the HOMO and LUMO energy of the donor and acceptor part almost independently. Bringing those orbitals closer in energy makes interactions between them stronger, but at the stone time the CT transition moves to a higher energy. Thus, the position of the CT band only weakly depends on the strength of the donor and acceptor used to construct the spiro compound. These two features are in contrast to the usual situation encountered in normally conjugated donor-acceptor systems (such as donor-acceptor substituted benzenes), where independent variations in the HOMO-LUMO gap are impractical, and increasing the donor or acceptor strength unavoidably shifts absorbtion maximal to longer wavelengths, placing the CT band in the position to absorb the harmonics generated by such a material. Such absorptive processes often lead to the destruction of the material. The spiro systems described here provide a new way to minimize that problem, which is considered to be one of the most difficult obstacles in the development of practical devices based on second order effects.

Simple modifications of the structure yield compounds with CT transitions covering the whole spectral range, from ultraviolet (320 nm) to visible (700 nm) The observed extinction coefficients for the allowed transitions are quite large, indicating that the orbital mixing induced by the spiroconjugation is quite strong. Thus, the CT-transition probability, that affects the magnitude of β (according to the two-state model), are quite respectable, with oscillator strengths comparable to that observed for normally conjugated systems.

Also in contrast with normally conjugated compounds which often have the ground state dipole moments fixed by the disposition of the acceptor and donor groups, the direction and magnitude of the ground state dipole moments of the spiro compounds can be manipulated by simple substitutions. The substituents placed off the long axis of the molecule (position 4 in the ninhydrin moiety, or positions 2 and 3 in the naphthyl moiety) allow for additional flexibility in the design of dipole moment components in directions other than the molecular axis. Finally, the variations of the ground state dipoles, or strategically-placed charged substituents allow for modifications of the crystal packing forces, that can lead to better alignment of the molecules in the solid state.

Another important feature that involves introduction of substituents into the donor or acceptor part is the resulting chirality (axial dissymmetry). The chirality of these systems is of the π type, i.e. the whole π-network is chiral. Such a construction leads to very strong interactions with polarized fight and can lead to development of NLO materials for polarized fight. Importantly, the π-chirality assures noncentrosymmetric crystal packing without diluting the chromophores, as is the case in existing NLO compounds where chirality is introduced by an add-on σ bonded groups that do not contribute to the non-linear response.

Specific examples of prepared compounds are listed in Schemes 2, 3 4, and 5. The preparation of these materials involved multistep syntheses, culminating in condensation of acceptor parts (substituted ninhydrins) with the appropriate donors. The details of the syntheses of the spiro compounds and their donor and acceptor components are provided below.

Unless otherwise noted, all materials were obtained from Aldrich Chemical Company, Inc., and used without purification. Reagent grade diethyl ether and tetrahydrofuran were distilled from potassium/benzophenone under argon immediately before use under anhydrous conditions. Reagent grade methylene chloride and spectrophotometric grade benzene were distilled from calcium hydride under argon immediately before use under anhydrous conditions. Aldrich anhydrous-grade (Sure-Seal) acetonitrile, dimethyl sulfoxide, dimethylformamide and dimethylacetamide were used for preparative work when needed in anhydrous form. The solvents used for UV-Vis and fluorescence spectroscopies were spectrophotometric grade and used without further purification. Pyridine was dried overnight over solid sodium hydroxide and then distilled under argon from the hydroxide onto 4 A molecular sieves for storage.

All $^1$H and $^{13}$C spectra were obtained using one of the following Bruker spectrometers: a AC-200 or WP-200 (200 MHz for proton), an AM-300 (300 MHz for proton) or a WP-360 (360 MHz for proton). $^1$H and $^{13}$C chemical shifts are reported in ppm with respect to tetramethylsilane (0.00 ppm). CDCl$_3$ was used as the solvent for $^1$H and $^{13}$C NMR, unless otherwise noted. All of the $^{13}$C spectra were recorded with high-power, broad-band decoupling.

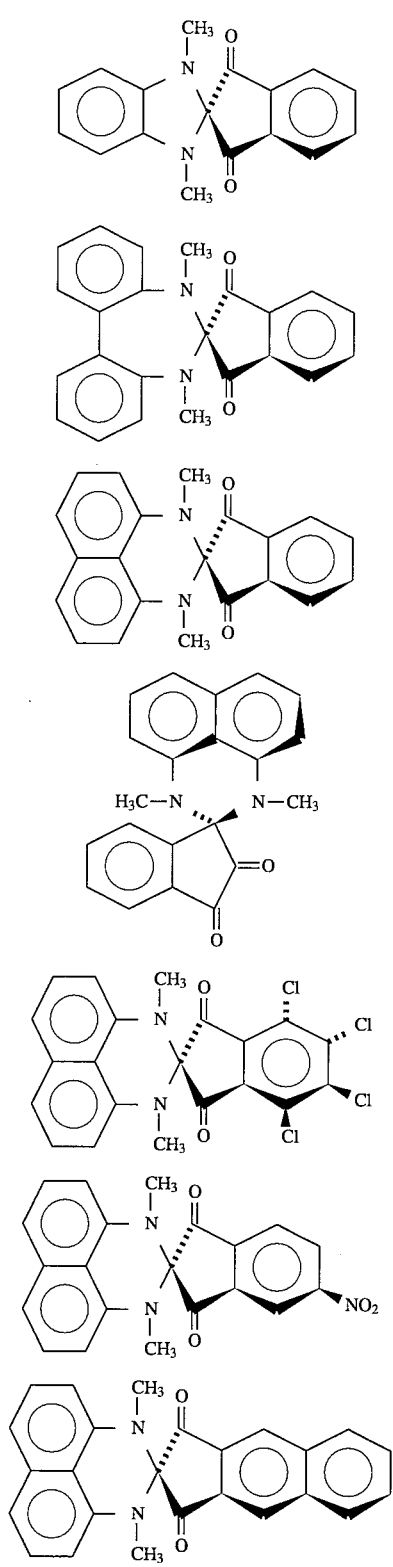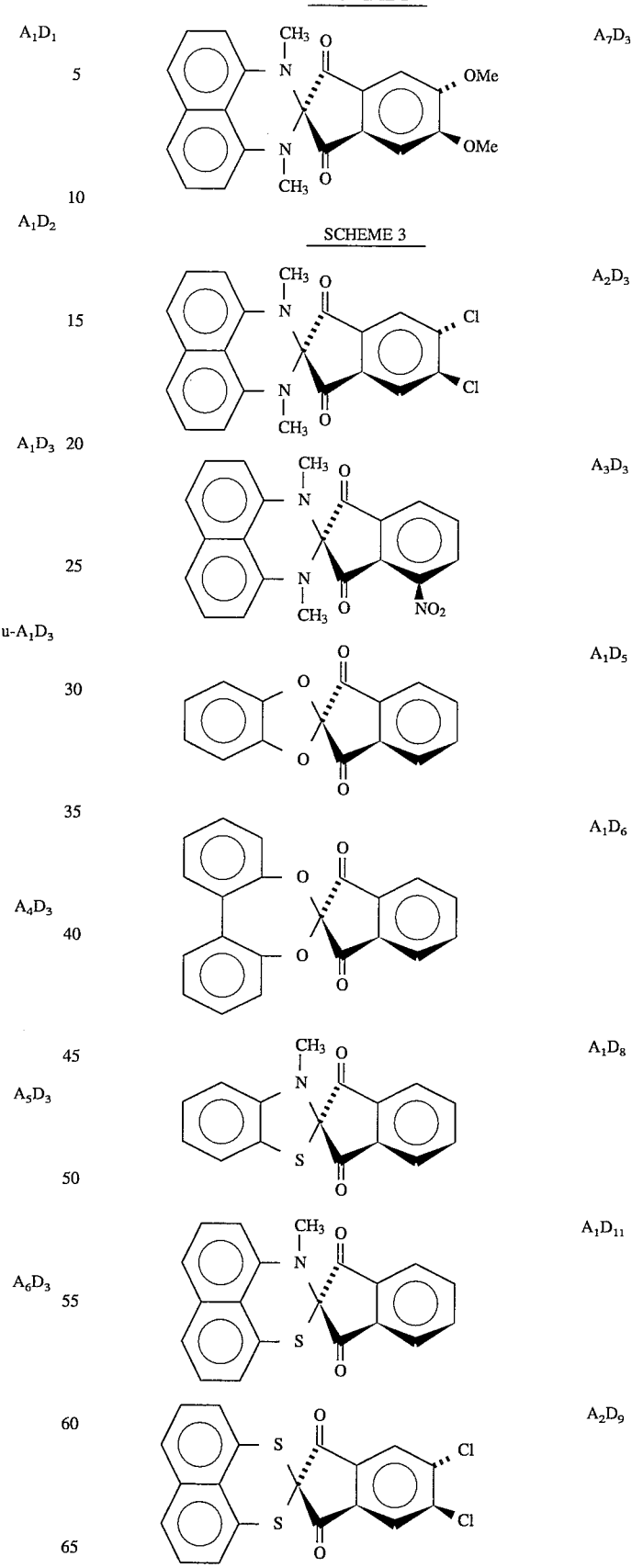

5,591,848
9
-continued
SCHEME 3
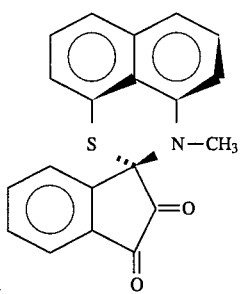
u-A₁D₁₁
SCHEME 4
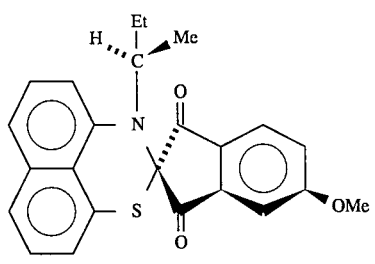
A₈D₁₂
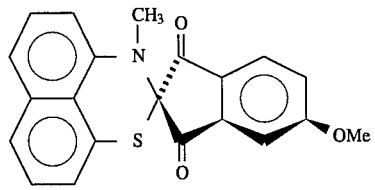
A₈D₁₁
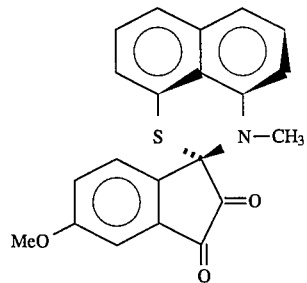
u-A₈-p-D₁₁
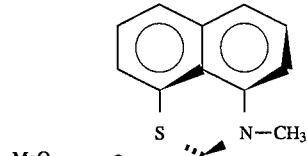
u-A₈-m-D₁₁
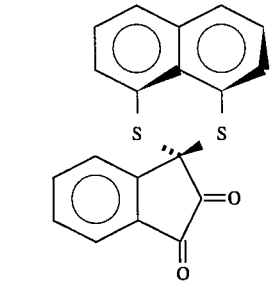
u-A₁D₉
10
-continued
SCHEME 4
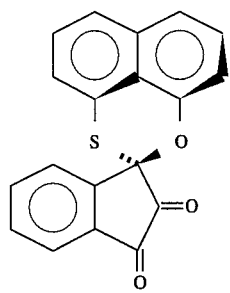
u-A₁D₁₀
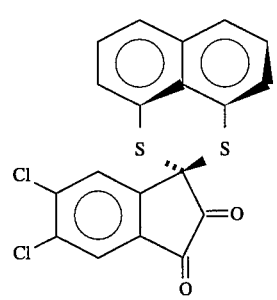
u-A₂D₉
SCHEME 5
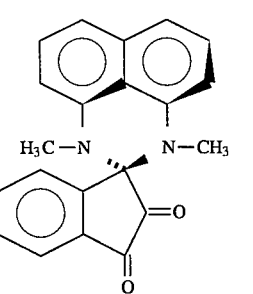
u-A₆D₃
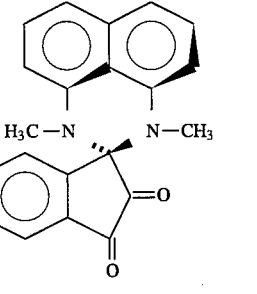
u-A₇D₃
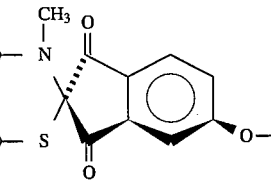
A₉D₁₁
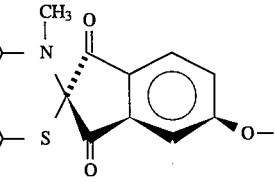
A₁₀D₁₁

-continued
SCHEME 5

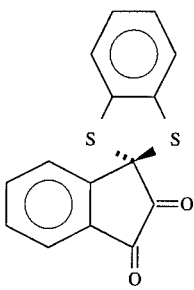

u-$A_1D_7$

Mass spectra were recorded using one of the following Kratos instuments: a MS-950 double-focussing mass spectometer in the electron-impact mode (reported as EI-MS) or a MS-25 double-focussing mass spectrometer for chemical ionization using isobutylene as the ionization gas (reported as CI-MS). Mass spectral data are expressed as m/e (intensity as the percent of the most abundant ion peak). All observed peaks with masses above 80 m/e and more intense than 10% of the most abundant ion peak as well as peaks judged to be of particular significance are reported.

All UV-Vis absorbance spectra were obtained using a Hewlett-Packard 8452A Diode Array Spectrometer at ambient temperatures. The cuvets used for these optical studies had a 1 cm pathlength unless mentioned otherwise.

Infrared spectra were obtained using either a Perkin Elmer Model 281B (reported as IR) or on a Perkin Elmer 1600 series FTIR spectrometer (reported as FTIR). Spectra of solids were recorded as pressed pellets prepared in a mini-press and are reported as FTIR (KBr) or IR (KBr). Spectra of oils were taken in an infrared solution cell in a suitable solvent and are reported as FTIR (solvent) or IR (solvent). The frequency of each peak is reported in $cm^{-1}$ and its intensity, relative to all other peaks in the spectrum, is denoted as being strong (s), medium (m) or weak (w). All peaks with intensity greater than ca. 10% of the largest peak observed in the spectrum as well as peaks judged to be of any notable significance are reported.

Preparative flash column chromatography was performed using Merck silica gel (230–400 mesh). Thin layer chromatography (TLC) was done on Merck precoated plates (60F-254) with layer thickness of 0.25 mm.

EXAMPLE 1

Preparation of Acceptor Compounds 1,2,3-Indantrione monohydrate (ninhydrin, $A_1$) was purchased from Aldrich Chemical Company.

5,6-Dichloroindan-1,3-dione (1) was prepared using the Knoevenagel reaction on 4,5-dichlorophthalic anhydride following the procedure outlined by Smith (Buckle, D. R.; Morgan, N. J.; Ross, J. W.; Smith, H.; Spicer, B. A. *J. Med. Chem.* 1973, 16, 1334).

5,6-Dichloroindan-2,2-dibromo-1,3-dione (2) was prepared by the enolic bromination of compound 1. Bromine (16 g, 0.1 mol) was added dropwise with stirring over a ten minute period to a solution of compound 1 (2.15 g, 0.01 mol) in 20 mL of dioxane. After stirring for two hours, the reaction mixture was poured slowly into 400 mL of water with vigorous stirring yielding a yellowish-brown solid. The solid was filtered after stirring for thirty minutes, washed with water and dried under vacuum to yield compound 2 (3.53 g, 94%) which was used for the next reaction without further purification. $^1$H NMR (CDCl$_3$, 200 MHz): 8.21 (s). EI-MS: 376 ($M^+$+6, 31%), 374 ($M^+$+4, 88%), 372 ($M^+$+2, 100%), 370 ($M^+$, 39%), 296 ($M^+$+5-Br, 12%), 294 ($M^+$+3-Br, 28%), 292 ($M^+$+1-Br, 17%), 267 ($M^+$+4-Br—CO, 17%), 265 ($M^+$+2-Br—CO, 38%), 263 ($M^+$-Br—CO, 25%).

5,6-Dichloroninhydrin ($A_2$) was prepared by the dimethyl sulfoxide hydrolysis of compound 2 using an approach of Joullié (Heffner, R. J.; Safaryn, J. E.; Joullié, M. M. *Tetrahedron Lett.* 1987, 28, 6085).

4-Nitroindan-1,3-dione (3) was prepared in a manner similar to that described for the preparation of compound 1.

4-Nitroninhydrin ($A_3$) was prepared according to the method of Neiland (Prikule, D. E.; Neiland, O. Y. *Zh. Org. Khim.* 1981, 17, 2119)

4,5,6,7-Tetrachloroindan-1,3-dione (5) was prepared in a manner similar to that described for compound 1.

4,5,6,7-Tetrachloroindan-2,2-dibromo-1,3-dione (6) was prepared by the enolic bromination of compound 5. as described for compound 2.

4,5,6,7-Tetrachloroninhydrin ($A_4$) was prepared in a manner similar to that described for compound $A_2$.

5-Nitroindan-1,3-dione (7) was prepared in a manner similar to that described for the preparation of compound 1.

5-Nitroindan-2,2-dibromo-1,3-dione (8) was prepared by the enolic bromination of compound 7 as described for preparation of compound 2.

5-Nitroninhydrin ($A_5$) was prepared in a manner similar to that described for compound $A_2$.

Diethyl naphthalene-2,3-dicarboxylate (9) was prepared by the esterification of the corresponding acid anhydride.

Benz[f]indan-1,3-dione (10) was prepared using the Claisen condensation on compound 9 following the procedure outlined by Smith (Buckle, D. R.; Morgan, N. J.; Ross, J. W.; Smith, H.; Spicer, B. A. *J. Med. Chem* 1973, 16, 1334).

2,2-Dibromo-benz[f]indan-1,3-dione (11) was prepared by the enolic bromination of compound 10 as described for compound 2.

Benz[f]ninhydrin ($A_6$) was prepared in a manner similar to that described for compound $A_2$.

5,6-Dimethoxyindan-2,2,3,3-tetrabromo-1-one (12) was prepared by the benzylic bromination followed by enolic bromination of 5,6-dimethoxyindan-1-one (Rf=0.17, 30% ethyl acetate in hexane). N-Bromosuccinimide (4.0 g, 22 mmol) and 20 mg of azobisisobutyronitrile were added to a solution of 5,6-dimethoxyindan-1one (2.0 g, 10 mmol) in 100 mL of carbon tetrachloride under an argon atmosphere. The mixture was heated at reflux and the reaction was followed by TLC and NMR. After 90 minutes of refluxing, there was no starting material left and NMR showed 5,6-dimethoxyindan-3,3-dibromo-1-one as the only product (Rf=0.52, 30% ethyl acetate in hexane). $^1$H NMR (CDCl$_3$, 200 MHz): 7.32 (s, 1H), 7.09 (s, 1H), 4.11 (s, 3H), 3.98 (s, 3H), 3.94 (s, 2H). The reaction mixture was cooled to room temperature and then a solution of bromine (3.5 g, 0.022 mol) in 20 mL of carbon tetrachloride was added dropwise over a 30 minute period with vigorous stirring. After the addition was complete, the mixture was brought to reflux and the reaction was followed by NMR. After 2–3 hours of refluxing, NMR showed compound 12 as the only product. The mixture was cooled to room temperature, filtered and the filtered solids were washed with carbon tetrachloride. The combined organic layers were then washed with water (3×100 mL), saturated sodium chloride solution (100 mL), dried over sodium sulfate and filtered. The filterate was removed under reduced pressure to yield compound 12 (5.07 g, 96%) as a yellow solid (Rf=0.52, 30% ethyl acetate in hexane) which was used for the next reaction without further purification. $^1$H NMR (CDCl$_3$, 200 MHz): 7.25 (s, 1H), 7.18 (s, 1H), 4.09 (s, 3H), 3.97 (s, 3H).

5,6-Dimethoxyindan-2,2-dibromo-1,3-dione (13) was prepared by the silver nitrate hydrolysis of compound 12. A solution of AgNO$_3$ (4.25 g, 0.025 mol) in 4 mL of water was added to a solution of compound 12 (5.08 g, 0.01 mol) in 50 mL of acetonitrile and the mixture was heated at reflux. A yellowish-white precipitate fell out of solution immediately and refluxing was continued for one hour. After cooling to room temperature, the mixture was filtered and the filtered solids were washed well with acetonitrile. The combined filterates were removed by rotary evaporation and the white solid thus obtained was suspended in 100 mL of methylene chloride. This solution was filtered to remove any remaining silver salts and the filterate was evaporated to yield compound 13 (3.41 g, 94%) as a white solid (Rf=0.37, 30% ethyl acetate in hexane) which was used for the next reaction without further purification. $^1$H NMR (CDCl$_3$, 300 MHz): 7.41 (s, 2H), 4.10 (s, 6H). $^{13}$C NMR (CDCl$_3$, 75 MHz): 186.4, 157.8, 130.6, 105.0, 57.0, 51.8. EI-MS: 366 (M$^+$+4, 49%),364(M$^+$+2, 100%),362(M$^+$, 51%),285 (M$^+$+2-Br, 32%),283 (M$^+$-Br, 30%), 255 (M$^+$-Br—CO, 23%).

5,6-Dimethoxyninhydrin (A$_7$) was prepared by the dimethyl sulfoxide hydrolysis of compound 13. as described for compound A$_2$.

5-Methoxyninhydrin (A$_8$) was prepared according to the method of Jouillié (Heffner, R. J.; Safaryn, J. E.; Joullié, M. M. *Tetrahedron Lett.* 1987, 28, 6085).

6-Hydroxyindan-1-one (16) was prepared by the demethylation of 6-methoxyindan-1-one (Rf=0.50, 30% ethyl acetate in hexane) using an approach similar to that of Gates (Gates, M.; Dickinson, C. L., Jr. *J. Org. Chem.* 1957, 22, 1398). Aluminum bromide (3.35 g, 12.6 mmol) was weighed under argon in an oven-dried flask and 6-methoxyindan-1-one (0.972 g, 6 mmol) was added to it. Dry benzene (40 mL) was added dropwise to this mixture and the resulting reddish-yellow solution was refluxed for four hours. The reaction mixture was cooled to room temperature after TLC showed no more starting material and 30 mL of 6N hydrochloric acid solution was added dropwise. The mixture was heated gently till the resulting solution was homogenous. The benzene layer was removed and the aqueous layer was extracted with ethyl acetate (3×20 mL). The combined organic layers were washed with water (50 mL), saturated sodium chloride solution (50 mL), dried over sodium sulfate and filtered. The filterate was removed under reduced pressure to yield 16 (3.41 g, 92%) as a grey solid (Rf=0.33, 30% ethyl acetate in hexane). White needles of compound 16 were obtained upon recrystallization from benzene. $^1$H NMR (acetone-d$_6$, 200 MHz): 8.62 (s, 1H, D$_2$O exchangeable), 7.39 (dd, J=8 Hz, 1 Hz, 1H), 7.14 (dd, J=8 Hz, 2 Hz, 1H), 7.03 (d, J=2 H z, 1H), 3.01 (m, 2H), 2.58 (m, 2H). EI-MS: 148 (M$^+$, 100%), 120 (M$^+$-CO, 93%), 92 (M$^+$-CO—2CH$_2$, 12%).

6-[O-Benzenesulfonyl]-hydroxyindan-1-one (17). Benzenesulfonyl chloride (0.128 mL, 1 mmol) was added dropwise to a solution of compound 16 (0.148 g, 1 mmol) in 2 mL of dry pyridine under an argon atmosphere. The resulting deep red solution was stirred overnight and then poured slowly with vigorous stirring into 3.5 mL of 15% hydrochloric acid to give a grey solid. After stirring for one hour, the solid was filtered, washed well with water and dried under vacuum to yield compound 17 (0.27 g, 93%). Upon recrystallization from 95% ethanol, colorless needles of compound 17 were obtained. $^1$H NMR (CDCl$_3$, 200 MHz): 7.85 (m, 2H), 7.72 (m, 1H), 7.53 (m, 3H), 7.29(m, 2H),3.11 (m, 2H),2.71 (m, 2H).

6-[O-Benzenesulfonyl]-hydroxyindan-3,3-dibromo-1-one (18) was prepared by the benzylic bromination of compound 17. N-Bromosuccinimide (0.35 g, 2 mmol) and azobisisobutyronitrile (5 mg) was added to a solution of compound 17 (0.27 g, 0.94 mmol) in 10 mL of carbon tetrachloride under an argon atmosphere. The mixture was heated at reflux and the reaction was followed by NMR. After one hour of refluxing, there was no starting material left and NMR showed compound 18 as the only product, which was used for the next reaction immediately. $^1$H NMR (CDCl$_3$, 200 MHz): 7.92 (m, 3H), 7.73 (m, 1H), 7.59 (m, 3H), 7.24 (m, 1H), 3.93 (s, 2H).

6-[O-Benzenesulfonyl]-hydroxyinden-2,3-dibromo-1-one (19). The mixture from the previous reaction was cooled to room temperature and then diluted to twice the initial volume with carbon tetrachloride. A solution of bromine (0.304 g, 1.91 mmol) in 2 mL of glacial acetic acid was added dropwise over a ten minute period with vigorous stirring. After the addition was complete, the mixture was brought to reflux and the reaction was followed by TLC and NMR. After 5–6 hours of refluxing, TLC showed no more starting material and NMR, after workup, showed compound 19 as the only product. The mixture was cooled to room temperature, filtered and the filtered solids were washed with carbon tetrachloride. The combined organic layers were then washed with 5% sodium hydroxide solution (30 mL), water (3×20 mL), saturated sodium chloride solution (30 mL), dried over sodium sulfate and filtered. The filterate was removed under reduced pressure to yield compound 19 (0.36 g, 86%) as a yellow solid (Rf=0.57, 30% ethyl acetate in hexane). $^1$H NMR (CDCl$_3$, 200 MHz): 7.88 (m, 2H), 7.71 (m, 1H), 7.56 (m, 2H), 7.16 (m, 2H), 7.04 (m, 1H). EI-MS: 446 (M$^+$+4, 8%), 444 (M$^+$+2, 15%), 442 (M$^+$, 8%), 305 (M$^+$+4-C$_6$H$_5$SO$_2$, 6%), 303 (M$^+$+2-C$_6$H$_5$SO$_2$, 11%), 301 (M$^+$-C$_6$H$_5$SO$_2$, 6%), 141 (C$_6$H$_5$SO$_2^+$, 100%).

5-[O-Benzenesulfonyl]-hydroxyninhydrin (A$_9$) was prepared by the dimethyl sulfoxide hydrolysis of compound 19. as described for compound A$_2$.

6-[O-Trifluoroacetyl]-hydroxyindan-1-one (20). To a solution of compound 16 (0.148 g, 1 mmol) in 2 mL of anhydrous methylene chloride, trifluoroacetic anhydride (0.70 mL, 5 mmol) was added dropwise with stirring under an argon atmosphere. The reaction was heated at reflux and followed by TLC. After 30–40 minutes, there was no more starting material left and the reaction was cooled to room temperature. The solvents were removed by rotary evaporation leaving a light brown oil which solidified after being placed under vacuum. The solid was recrystallized from hexane to yield compound 20 (0.21 g, 86%) as colorless needles (Rf=0.56, 40% ethyl acetate in hexane). The filterate from the recrystallization was evaporated under reduced pressure to give 12 mg of the starting phenol. $^1$H NMR (CDCl$_3$, 200 MHz): 7.58 (m, 2H), 7.42 (dd, J=8 Hz, J=2 Hz, 1H), 3.18 (m, 2H), 2.77 (m, 2H).

6-[O-Trifluoroacetyl]-hydroxyindan-3,3-dibromo-1-one (21) was prepared in a manner similar to that used for compound 18.

6-Hydroxyinden-2,3-dibromo-1-one (22). The mixture from the previous reaction was cooled to room temperature and then diluted to twice the initial volume with carbon tetrachloride. A solution of bromine (0.103 g, 0.64 mmol) in 2 mL of glacial acteic acid was added dropwise over a ten minute period with vigorous stirring. After the addition was complete, the mixture was brought to reflux. The reaction was followed by NMR, which showed 6-[O-trifluoroacetyl]-hydroxyinden-2,3-dibromo-1-one (0.23 g, 91%) as the only product after 1–2 hours of refluxing. $^1$H NMR (CDCl$_3$, 200 MHz): 7.41 (m, 1H), 7.29 (m, 2H). CI-MS: 402 (M$^+$+4, 50%), 401 (MH$^+$+2, 27%), 400 (M$^+$+2, 100%), 399 (MH$^+$, 35%), 398 (M$^+$, 51%), 321 (M$^+$+2-Br, 16%), 319 (M$^+$-Br, 23%). The mixture was cooled to room temperature, filtered and the filtered solids were washed with carbon tetrachloride. The combined organic layers were then washed with 5% sodium hydroxide solution (25 mL), water (3×25 mL), saturated sodium chloride solution (30 mL), dried over sodium sulfate and filtered. The filterate was removed under reduced pressure to yield a colorless oil. This oil was purified by column chromatography using a mixture of 15% ethyl acetate in hexane as the eluant. The trifluoroacetyl group was hydrolysed during the course of the seperation to yield compound 22 (0.106 g, 67%) as a reddish-brown solid (Rf=0.38, 20% ethyl acetate in hexane). $^1$H NMR (acetone-d$_6$, 200 MHz): 9.28 (s, 1H, D$_2$O exchangeable), 7.11 (d, J=8 Hz, 1H), 6.94 (d, J=2 Hz, 1H), 6.90 (dd, J=8 Hz, J=2 Hz, 1H). EI-MS: 306 (M$^{+b\ +4,\ 39}$%), 304 (M$^+$+2, 76%), 302 (M$^+$, 41%), 225 (M$^+$+2-Br, 97%), 223 (M$^+$-Br, 100%), 197 (M$^+$+2-Br—CO, 33%), 195 (M$^+$-Br—CO, 33%).

6-[O-(+)-10-Camphorsulfonyl]-hydroxyinden-2,3-dibromo-1-one (23) was prepared using an approach of Wolfrom (Wolfrom, W. L.; Koos, E. W.; Bhat, H. R. *J.Org.Chem.* 1967, 32, 1058).

5-[O-(+)-10-Camphorsulfonyl]-hydroxyninhydrin (A$_{10}$) was prepared by the dimethyl sulfoxide hydrolysis of compound 23 as described for compound A$_2$.

EXAMPLE 2

Preparation of Donor Compounds

N,N'-Dimethyl-1,2-phenylenediamine (D$_1$) was prepared by the method of Cheeseman (Cheeseman, G. W. H. *J.Chem.Soc.* 1955, 3308.)

N,N'-Dimethyl-2,2'-diaminobiphenyl (D$_2$) was prepared by the method analogous to that used for preparation of compound D$_1$.

1,8-Bis(methylamino)naphthalene (D$_3$) was prepared according to the method of Pozharskii (Pozharskii, A. F.; Suslov, A. N.; Starshikov, N. M.; Popova, L. L.; Klyuev, N. A.; Adanin, V. A. *Zh.Org.Khim.* 1980, 16, 2216).

2-(Methylamino)-benzenethiol (D$_8$) was prepared using an approach of Kiprianov (Kiprianov, A. I.; Pazenko, Z. N. *Zhur.Obshchei.Khim.* 1949, 19, 1523).

Disodium 8,8'-dithiodi-1,1'-naphthalenesulfonate (33) was prepared according to the procedure of Zweig and Hoffmann (Zweig, A.; Hoffmann, A. K. *J. Org. Chem.* 1965, 30, 3997).

Naphtho[1,8-cd]-1,2-dithiol 1,1 dioxide (34) was prepared according to the described procedure (Allen, C. F. H.; Mackay, D. D. *Organic Syntheses* Coll. Vol. II; Blatt, A. H., Ed.; John Wiley and Sons, New York, N.Y., 1943, p 580.)

Naphthalene-1,8-dithiol (D$_9$) was prepared by the method of Price and Smiles (Price, W. B.; Smiles, S. *J. Chem. Soc.* 1928, 2372).

Di-8-hydroxynaphthyl disulfide (35) was prepared by the lithium aluminum hydride (LAH) reduction of 1,8-naphthosultone (Rf=0.48, 30% ethyl acetate in hexane) using an approach of Knox and Pauson (Knox, G. R.; Pauson, P. L. *J. Chem. Soc.* 1958, 692).

1 8-Hydroxy-1-naphthalenethiol (D$_{10}$) was prepared by the sodium borohydride reduction of 35 using a method of D'Amico (D'Amico, D'Amico, J. J. *J. Org. Chem.* 1961, 26, 3436)

N-Methyl-1,8-naphthosultam (36) was prepared by the alkylation of 1,8-naphthosultam (Rf=0.38, 30% ethyl acetate in hexane; Rf=0.11, 60% methylene chloride in hexane) with iodomethane. A solution of sodium hydroxide (0.42 g, 10.5 mmol) in 10 mL of water was added, with stirring, to a solution of 1,8-naphthosultam (2.05 g, 10 mmol) in 10 mL of dimethylacetamide under an argon atmosphere. The mixture became warm upon addition of base and was allowed to cool to room temperature. Iodomethane (0.65 mL, 10.5 mmol) was then added to the mixture and the resulting solution was stirred for two hours. Reaction progress was followed by TLC and the reaction was stopped upon complete disappearance of starting material. The reaction mixture was poured slowly into 150 mL of water, with vigorous stirring, yielding a greyish-white solid. After stirring for thirty minutes, the solid was filtered, washed with water and dried under vacuum. Upon recrystallization from 20% ethyl acetate in hexane, white crystals of compounds 36 (1.56 g, 71% ) were obtained (Rf=0.55, 30% ethyl acetate in hexane; Rf=0.36, 60% methylene chloride in hexane). $^1$H NMR (CDCl$_3$, 300 MHz): 8.07 (dd, J=8 Hz, J=1 Hz, 1H), 7.97 (dd, J=7 Hz, J=1 Hz, 1H), 7.75 (dd, J=8 Hz, J=7 Hz, 1H), 7.55 (t, J=8 Hz, 1H), 7.46 (dd, J=8 Hz, J=1 Hz, 1H), 6.72 (dd, J=7 Hz, J=1 Hz, 1H), 3.38 (s, 3H). EI-MS: 219 (M$^+$, 10%), 155 (M$^+$-SO$_2$, 5%), 126 (M$^+$-NMe—SO$_2$, 3%), 64 (SO$_2^+$, 17%).

8-(Methylamino)-1-naphthalenethiol (D$_{11}$) was prepared by the LAH reduction of compound 36 using a method similar to that described for compound 35.

(S)-O-(Toluene-p-sulfonyl)-2-butanol (37) A solution of (S)-(+)-2-butanol (0.1 mL, 1.1 mol) and toluene-p-sulfonyl chloride (0.207 g, 1.1 mmol) in 1.5 mL of anhydrous pyridine was stirred overnight under an argon atmospere. The reaction mixture was then slowly poured into 4 mL of 15% hydrochloric acid, with vigorous stirring. After stirring for 30 minutes, the solution was extracted with methylene chloride (3×5 mL). The combined organic extracts were washed with saturated sodium chloride solution (10 mL), dried over sodium sulfate and filtered. The filterate was evaporated under reduced pressure to yield compound 37 (0.23 g, 89%) as a white solid, (Rf=0.59, 15% ethyl acetate in hexane), which was dried under vacuum and then used for the next reaction without further purification. $^1$H NMR (CDCl$_3$, 200 MHz): 7.80 (d, J=8 Hz, 2H), 7.33 (d, J=8 Hz, 2H), 4.56 (sextet, J=6 Hz, 1H), 2.44 (s, 3H), 1.59 (m, 2H), 1.24 (d, J=6 Hz, 3H), 0.81 (t, J=7 Hz, 3H).

N-(R)-sec-Butyl-1,8-naphthosultam (38). A solution of 1,8-naphthosultam (0.27 g, 1.32 mmol, Rf=0.30, 20% ethyl acetate in hexane) in 5 mL of anhydrous THF was slowly added to a 60% dispersion of sodium hydride in mineral oil (0.053 g, 1.32 mmol of NaH) under an argon atmosphere. The resulting greenish-brown solution was stirred at room temperature for ten minutes, and then a solution of compound 37 (0.23 g, 1 mmol) in 10 mL of anhydrous THF was added dropwise, with stirring, over a twenty minute period. After the addition was complete, the resulting mixture was refluxed for six hours. The reaction progress was followed by TLC and the reaction was stopped upon disappearance of compound 37, (Rf=0.67, 20% ethyl acetate in hexane). After cooling to room temperature, water (30 mL) was added and the resulting solution was extracted with methylene chloride (3×20 mL). The combined organic extracts were washed with saturated sodium chloride solution (30 mL), dried over sodium sulfate and filtered. The filtrate was evaporated under reduced pressure to yield a yellow oil. The oil was purified by column chromatography using a mixture of 15% ethyl acetate in hexane as the eluant. After the purification, compound 38 (0.101 g, 38%) was obtained as a white solid (Rf=0.56, 20% ethyl acetate in hexane). $^1$H NMR (CDCl$_3$, 200 MHz): 8.04 (dd, J=8 Hz, J=1 Hz, 1H), 7.94 (dd, J=7 Hz, J=1 Hz, 1H), 7.72 (dd, J=8 Hz, J=7 Hz, 1 H), 7.43 (m, 2H), 6.81 (dd, J=7 Hz, J=1 Hz, 1H), 4.20 (sextet, J=7 Hz, 1H), 2.25–1.83 (m, 2H), 1.60 (d, J=7 Hz, 3H), 1.05 (t, J=7 Hz, 3H).

8-N-(R)-sec-Butylamino-1-naphthalenethiol (D$_{12}$) was prepared by the LAH reduction of compound 38 using a method similar to that described for preparation of compound D$_{11}$.

EXAMPLE 3

Preparation of Spiro Compounds

General procedure: A donor compound was condensed with an equimolar amount of an acceptor compound using benzene (spectrophotometric grade, dried over 4 A sieves for at least one day before use) as solvent and p-toluenesulfonic acid as catalyst. The reaction vessel was equipped with a Dean-Stark trap for azeotropic removal of water as it is formed during the reaction. Typically, the donor compound was added to a solution of the acceptor compound and catalyst (ca. 5–10 mg) under an argon atmosphere. The scale of this reaction varied from 10 mg to 1 g each of donor and acceptor compounds. The solution was brought to reflux and the reaction was followed by TLC using an appropriate amount of ethyl acetate in hexane as the eluant. The reaction was usually complete (marked by disappearance of starting materials on TLC) after 2–5 hours of refluxing. The solvent was removed under reduced pressure and the products were isolated as highly colored solids using flash column chromatography on silica gel with an appropriate amount of ethyl acetate in hexane as the eluant.

Compound A$_1$D$_1$: The reaction was carried out using 1.00 g of compound D$_1$ and an equimolar amount of compound A$_1$. The pure compound was isolated after column chromatography (Rf=0.42, 40% ethyl acetate in hexane) in 60% yield. Upon recrystallization from benzene, deep purple needles of compound A$_1$D$_1$ were obtained, mp 142° C., $\lambda_{max}$=552 nm (CH$_2$Cl$_2$). $^1$H NMR (CDCl$_3$, 200 MHz): 8.10–7.98 (m, 4H), 6.68–6.65 (m, 2H), 6.33–6.30 (m, 2H), 2.61 (s, 6H). $^{13}$C NMR (CDCl$_3$, 50 MHz): 198.2, 140.6, 140.5. 137.4, 123.5, 119.3, 104.4, 87.6, 30.7. EI-MS: 278 (M$^+$, 27%), 249 (M$^+$-NCH$_3$, 23%), 221 (M$^+$-NCH$_3$—CO, 100%). FTIR (KBr): 3070 (w), 2878 (w), 2813 (w), 1747 (m), 1717 (s), 1598 (m), 1503 (s), 1403 (w), 1324 (m), 1268 (w), 1238 (m), 1218 (m), 1115 (m), 1015 (m), 932 (s), 878 (w), 774(m), 741 (s), 711 (m), 676 (w), 607 (w),561 (w).

Compound A$_1$D$_2$: The reaction was carried out using 1.00 g of compound D$_2$ and an equimolar amount of compound A$_1$. After column chromatography, the product was isolated in a 76% yield (Rf=0.50, 40% ethyl acetate in hexane). Orange-yellow leaflets of compound A$_1$D$_2$ were obtained upon recrystallization from 95% ethanol, mp 202° C., $\lambda_{max}$=420 nm (CH$_2$Cl$_2$). $^1$H NMR (CDCl$_3$, 300 MHz): 8.05–7.95 (m, 4H), 7.42–7.35 (m, 4H), 7.30–7.25 (m, 2H), 7.14 (dd, J=8 Hz, 1 Hz, 2H), 2.56 (s, 6H). $^{13}$C NMR (CDCl$_3$, 90 MHz): 200.8, 145.3, 139.2, 137.0, 136.3, 128.2, 128.0, 124.8, 122.8, 121.3, 90.7, 36.7. EI-MS: 354 (M$^+$, 100%), 339 (M$^+$-CH$_3$, 5%), 325 (M$^+$-NCH$_3$, 13%), 297 (M$^+$-NCH$_3$—CO, 27%). FTIR (KBr): 2980 (w), 2860 (w), 1743 (m), 1709 (s), 1590 (w), 1554 (w), 1500 (w), 1442 (m), 1315 (w), 1254 (m), 1190 (w), 1110 (w), 931 (m), 760 (m), 694 (w), 626 (w).

Compound A$_1$D$_3$: The reaction was carried out using 1.00 g of compound D$_3$ and an equimolar amount of compound A$_1$. The pure compound was isolated in 64% yield after column chromatography (Rf=0.51, 40% ethyl acetate in hexane). Recrystallization from 95% ethanol gave reddish-brown needles of compound A$_1$D$_3$, mp 293° C. $\lambda_{max}$414 nm (CH$_2$Cl$_2$) $^1$H NMR (CDCl$_3$, 360 MHz): 8.06–7.97 (m, 4H), 7.35 (dd, J=8 Hz, J=7 Hz, 2H), 7.31 (dd, J=8 Hz, J=1 Hz, 2H), 6.64 (dd, J=7 Hz, J=1 Hz, 2H), 2.80 (s, 6H). $^{13}$C NMR (CDCl$_3$, 50 MHz): 199.4, 140.9, 140.3, 137.2, 133.3, 126.7, 123.3, 119.2, 113.2, 105.1, 76.9, 34.5. EI-MS: 328 (M$^+$, 36%), 299 (M$^+$-NCH$_3$, 5%), 271 (M$^+$-NCH$_3$—CO, 100%); CI-MS 329 (M$^+$+1, 84%), 328 (M$^+$, 100%), 300 (M$^+$-CO, 5%), 271 (M$^+$-NCH$_3$—CO, 29%). FTIR (KBr): 2880 (w), 2810 (w), 1745 (m), 1702 (s), 1582 (s), 1478 (m), 1422 (m), 1390 (w), 1335 (w), 1264 (m), 1220 (w), 1172 (w), 986 (w), 804 (m), 752 (m), 715 (w), 640 (w).

Compound u-A$_1$D$_3$: The reaction was carried out using 1.00 g of compound D$_3$ and an equimolar amount of compound A$_1$. The pure compound was isolated after column chromatography (Rf=0.63, 40% ethyl acetate in hexane) in 12% yield. Upon recrystallization from 20% ethyl acetate in hexane, deep purple needles of compound u-A$_1$D$_3$ were obtained $\lambda_{max}$=552 nm (CH$_2$Cl$_2$). $^1$H NMR (CDCl$_3$, 200 MHz): 8.09 (dd, J=7 Hz, J=1 Hz, 1H), 7.93 (td, J=8 Hz, J=1 Hz, 1H), 7.75 (m, 2H), 7.38 (m, 4H), 6.66 (dd, J=7 Hz, J=2 Hz, 2H), 2.63 (s, 6H). $^{13}$C NMR (CDCl$_3$, 50 MHz): 205.8, 184.2, 149.2, 141.1, 139.5, 139.0, 133.4, 131.1, 127.2, 126.9, 124.6, 119.4, 112.6, 105.4, 74.6, 34.7. EI-MS: 328 (M$^+$, 1%), 300 (M$^+$-CO, 14%), 272 (M$^+$-2CO, 32%), 271 (M$^+$-2CO—H, 100%), 257 (M$^+$-2CO—CH$_3$, 9%), 256 (M$^+$-2CO—CH$_3$—H, 43%). CI-MS: 329 (MH$^+$, 100%), 328 (M$^+$, 3%), 301 (MH$^+$-CO, 18%), 300 (M$^+$-CO, 44%), 272 (M$^+$-2CO, 52%), 271 (M$^+$-NCH$_3$—CO, 49%), 256 (M$^+$-NCH$_3$—CO—CH$_3$, 13%).

Compound A$_2$D$_3$: The reaction was carried out using 0.32 g of compound D$_3$ and an equimolar amount of compound A$_2$. The pure compound (Rf=0.75, 40% ethyl acetate in hexane) was isolated after column chromatography, using 15% ethyl acetate in hexane as the eluant, in 62% yield. Upon recrystallization from 20% ethyl acetate in hexane, reddish-brown needles of compound A$_2$D$_3$ were obtained. $\lambda_{max}$=430 nm (CH$_2$Cl$_2$) $^1$H NMR (CDCl$_3$, 200 MHz): 8.10 (s, 2H), 7.38 (m, 4H), 6.65 (dd, J=6 Hz, J=2 Hz, 2H), 2.80 (s, 6H). $^{13}$C NMR (CDCl$_3$, 50 MHz): 197.3, 142.8, 140.5, 138.7, 133.3, 126.7, 125.1, 119.7, 113.2, 105.6, 77.2, 34.6. EI-MS: 400 (M$^+$+4, 7%), 399 (M$^+$+3, 10%), 398 (M$^+$+2, 30%), 397 (M$^+$+1, 12%) 396 (M$^+$, 44%), 343 (M$^+$+4-NCH$_3$—CO, 13%), 342 (M$^+$+3-NCH$_3$—CO, 16 %), 341 (M$^+$+2-NCH$_3$—CO, 60%), 340 (M$^+$+1-NCH$_3$—CO, 23%), 339 (M$^+$NCH$_3$—CO, 89%), 328 (M$^+$+4-NCH$_3$—CO—CH$_3$, 4%), 327 (M$^+$+3-NCH$_3$—CO—CH$_3$, 5%), 326 (M$^+$+2-NCH$_3$—CO—CH$_3$, 18%), 325 (M$^+$+1-NCH$_3$—CO—CH$_3$, 14%), 324 (M$^+$-NCH$_3$—CO—CH$_3$, 24%).

Compound A$_3$D$_3$: The reaction was carried out using 0.372 g of compound D$_3$ and an equimolar amount of compound A$_3$. The pure compound (Rf=0.32, 40% ethyl acetate in hexane) was isolated after column chromatography; using 20% ethyl acetate in hexane as the eluant, in 38% yield. $\lambda_{max}$=456 nm (CH$_2$Cl$_2$) $^1$H NMR (CDCl$_3$, 300 MHz): 8.19 (m, 2H), 8.01 (t, J=8 Hz, 1H), 7.35 (m, 4H), 6.68 (dd, J=7 Hz, J=2 Hz, 2H), 2.85 (s, 6H). $^{13}$C NMR (CDCl$_3$, 50 MHz): EI-MS: 373 (M$^+$, 24%), 343 (M$^+$-2CH$_3$, 9%), 299

($M^+$-$NO_2$—CO, 72%), 284 ($M^+$-$NO_2$— CO—$CH_3$, 19%), 270 ($M^+$-$NO_2$—CO—$NCH_3$, 15%), 256 ($MH^+$-$NO_2$—CO—$NCH_3$—$CH_3$, 100%), 255 ($M^+$-$NO_2$—CO—$NCH_3$—$CH_3$, 88%).

Compound $A_4D_3$: The reaction was carried out using 0.46 g of compound $D_3$ and an equimolar amount of compound $A_4$. The pure compound (Rf=0.48, 15% ethyl acetate in hexane) was isolated after column chromatography, using 10% ethyl acetate in hexane as the eluant, in 41% yield. $\lambda_{max}$=452 nm ($CH_2Cl_2$) $^1$H NMR ($CDCl_3$, 200 MHz): 7.37 (m, 4H), 6.68 (dd, J=6 Hz, J=3 Hz, 2H), 2.85 (s, 6H). CI-MS: 471 ($M^+$+7, 7%), 470 ($M^+$+6, 12%), 469 ($M^+$+5, 23%), 468 ($M^+$4, 33%), 467 ($M^+$+3, 40%), 466 ($M^+$+2, 51%), 465 ($M^+$+1, 26%), 464 ($M^+$, 31%), 377 ($M^+$+5-$NCH_3$—CO—Cl, 4%), 376 ($M^+$+4-$NCH_3$—CO—Cl, 3%), 375 ($M^+$+3-$NCH_3$—CO—Cl, 10%), 374 ($M^+$+2-$NCH_3$—CO—Cl, 4%), 373 ($M^+$+1-$NCH_3$—CO—Cl, 10%), 372 ($M^+$-$NCH_3$—CO—Cl, 3%).

Compound $A_5D_3$: The reaction was carried out using 0.18 g of compound $D_3$ and an equimolar amount of compound $A_5$. The pure compound (Rf=0.65, 40% ethyl acetate in hexane) was isolated after column chromatography, using 30% ethyl acetate in hexane as the eluant, in 48% yield. $\lambda_{max}$=448 nm ($CH_2Cl_2$) $^1$H NMR ($CDCl_3$, 360 MHz): 8.83 (d, J=2 Hz, 1H), 8.78 (dd, J=8 Hz, J=2 Hz, 1H), 8.21 (d, J=8 Hz, 1H), 7.39 (m, 4H), 6.69 (dd, J=7 Hz, J=2 Hz, 2H), 2.84 (s, 6H). $^{13}$C NMR ($CDCl_3$, 50 MHz): EI-MS: 373 ($M^+$, 74%), 344 ($M^+$-$NCH_3$, 6%), 316 ($M^+$-$NCH_3$—CO, 100%), 301 ($M^+$-$NCH_3$—CO—$CH_3$, 11%), 284 ($M^+$-$NO_2$—CO—$CH_3$, 3%), 270 ($M^+$-$NO_2$—CO—$NCH_3$, 31%), 256 ($MH^+$-$NO_2$—CO—$NCH_3$—$CH_3$, 11%), 255 ($M^+$-$NO_2$—CO—$NCH_3$—$CH_3$, 25%).

Compound $A_6D_3$: The reaction was carried out using 0.93 g of compound $D_3$ and an equimolar amount of compound $A_6$. The pure compound (Rf=0.24, 15% ethyl acetate in hexane) was isolated after column chromatography, using 20% ethyl acetate in hexane as the eluant, in 53% yield. Recrystallization from 20% ethyl acetate in hexane gave reddish-brown needles of compound $A_6D_3$. $\lambda_{max}$=452 nm ($CH_2Cl_2$) $^1$H NMR ($CDCl_3$, 200 MHz): 8.59 (s, 2H), 8.20–8.16 (m, 2H), 7.82–7.77 (m, 2H), 7.43–7.31 (m, 4H), 6.65 (dd, J=7 Hz, J=2 Hz, 2H), 2.84 (s, 6H). $^{13}$C NMR ($CDCl_3$, 50 MHz): 199.5, 141.0, 137.1, 135.1, 133.3, 130.9, 130.4, 128.3, 126.7, 124.6, 119.2, 105.1, 77.5, 34.5. EI-MS: 378 ($M^+$, 55%), 363 ($M^+$-$CH_3$, 3%), 350 $M^+$-CO, 4%), 349 ($M^+$-$NCH_3$, 7%), 321 ($M^+$-$NCH_3$—CO, 100%), 306 ($M^+$-$NCH_3$—CO—$CH_3$, 33%).

Compound u-$A_6D_3$: The reaction was carried out using 0.93 g of compound $D_3$ and an equimolar amount of compound $A_6$. The pure compound (Rf=0.32, 15% ethyl acetate in hexane) was isolated after column chromatography, using 20% ethyl acetate in hexane as the eluant, in 14% yield. Upon recrystallization from 20% ethyl acetate in hexane, deep purple needles of compound u-$A_6D_3$ were obtained,. $\lambda_{max}$=590 nm ($CH_2Cl_2$) $^1$H NMR ($CDCl_3$, 200 MHz): 8.67 (s, 1H), 8.24 (s, 1H), 8.16 (dd, J=7 Hz, J=1 Hz, 1H), 7.98 (dd, J=8 Hz, J=1 Hz, 1H), 7.76 (m, 2H), 7.43–7.31 (m, 4H), 6.68 (dd, J=7 Hz, J=2 Hz, 2H), 2.67 (s, 6H). $^{13}$C NMR ($CDCl_3$, 50 MHz):. EI-MS: 378 ($M^+$, 2%), 350 ($M^+$-CO, 15%), 322 ($M^+$-2CO, 51%), 321 ($M^+$-2CO—H, 100%), 307 ($M^+$-2CO—$CH_3$, 10%), 306 ($M^+$-2CO—$CH_3$—H, 35%), 293 ($M^+$-2CO—$NCH_3$, 4%), 292 ($M^+$-2CO—$NCH_3$—H, 11%).

Compound $A_7D_3$: The reaction was carried out using 0.36 g of compound $D_3$ and an equimolar amount of compound $A_7$. The pure compound (Rf=0.60, 50% ethyl acetate in hexane) was isolated after column chromatography, using 40% ethyl acetate in hexane as the eluant, in 55% yield. Upon recrystallization from acetone, orange needles of compound $A_7D_3$ were obtained. $\lambda_{max}$=370 nm ($CH_2Cl_2$) $^1$H NMR ($CDCl_3$, 300 MHz): 7.37 (s, 2H), 7.35–7.27 (m, 4H), 6.60 (dd, J=7 Hz, J=1Hz, 2H), 4.04 (s, 6H), 2.80 (s, 6H). $^{13}$C NMR ($CDCl_3$, 50 MHz): 198.2, 157.1, 141.1, 135.9, 133.4, 126.7, 118.8, 113.2, 104.6, 103.1, 77.2, 56.9, 34.2. EI-MS: 388 ($M^+$, 72%), 373 ($M^+$-$CH_3$, 3%), 360 ($M^+$-CO, 2%), 359 ($M^+$-$NCH_3$, 4%), 331 ($M^+$-$NCH_3$—CO, 100%), 316 ($M^+$-$NCH_3$—CO—$CH_3$, 9%), 301 ($M^+$-$NCH_3$—CO—2$CH_3$, 10%).

Compound u-$A_7D_3$: The reaction was carried out using 0.36 g of compound $D_3$ and an equimolar amount of compound $A_7$. The pure compound (Rf=0.68, 50% ethyl acetate in hexane) was isolated after column chromatography, using 40% ethyl acetate in hexane as the eluant, in 7% yield. Upon recrystallization from acetone, deep purple needles of compound u-$A_7D_3$ were obtained,. $\lambda_{max}$=570 nm ($CH_2Cl_2$) $^1$H NMR ($CDCl_3$, 300 MHz): 7.47 (s, 2H), 7.42–7.36 (m, 4H), 7.13 (s, 2H), 6.65 (dd, J=7 Hz, J=1 Hz, 2H), 4.04 (s, 3H), 2.65 (s, 6H). $^{13}$C NMR ($CDCl_3$, 50 MHz): 204.2, 181.3, 158.2, 151.3, 145.2, 140.3, 134.4, 132.6, 126.0, 118.3, 111.6, 105.7, 104.4, 103.6, 73.9, 56.2, 55.7, 33.7. EI-MS: 388 ($M^+$, 2%), 360 ($M^+$-CO, 11%), 332 ($M^+$-2CO, 30%), 331 ($M^+$-2CO—H, 100%), 317 ($M^+$-2CO—$CH_3$, 29%), 316 ($M^+$-2CO—$CH_3$—H, 10%), 303 ($M^+$-2CO—$NCH_3$, 5%), 302 ($M^+$-2CO—$NCH_3$—H, 12%).

2,2'-Spiro-1,3-dioxobiindan (39). Benzene (100 mL, spectrophotometric grade, dried over 4 A sieves for at least one day before use) was added to a mixture of 2-indanone (1.32 g, 0.01 mol), catechol ($D_5$, 5.5 g, 0.05 mol) and p-toluenesulfonic acid (50 mg) under an argon atmosphere. The reaction vessel was equipped with a Dean-Stark trap for azeotropic removal of water. The solution was brought to reflux and the reaction was followed by TLC using a mixture of 30% methylene chloride in hexane as the eluant. After refluxing overnight, the reaction mixture was cooled to room temperature and then washed with 5% sodium hydroxide solution (2×50 mL) to remove excess catechol and residual p-toluenesulfonic acid. The benzene layer was seperated and then washed with saturated sodium chloride solution (50 mL), dried over sodium sulfate, filtered and the solvent was removed under reduced pressure to yield a dark brown oil. The oil was purified by column chromatography using a mixture of 30% methylene chloride in hexane as the eluant to yield compound 39 (1.74 g, 78%) as a greyish white solid. $^1$H NMR ($CDCl_3$, 200 MHz): 7.23 (m, 4H), 6.79 (m, 4H), 3.47 (s, 4H). EI-MS: 224 ($M^+$, 38%), 210 ($M^+$-$CH_2$, 1%), 194 ($M^+$-$CH_2$—O, 2%), 148 ($M^+$-$C_6H_4$, 5%), 132 ($M^+$-$C_6H_4$—O, 10%), 116 $M^+$-$C_6H_4$—2O, 94%), 115 ($M^+$-$C_6H_4$—2O—H, 100%), 104 ($M^+$-$C_6H_4$—2O—C, 27%).

2,2'-Spiro-1,3-dioxo-1',1',3',3'-tetraabromobiindan (40) was prepared by the benzylic bromination of compound 39. N-Bromosuccinimide (8.90 g, 50 mmol) and azobisisobutyronitrile (20 mg) were added to a solution of 39 (1.12 g, 5.0 mmol) in 50 mL of carbon tetrachloride under an argon atmosphere. The mixture was heated at reflux and the reaction progress was followed by TLC and NMR. Azobisisobutyronitrile (10 mg) was added every six hours to the reaction mixture. After 2 days of refluxing, there was no starting material left by TLC, and NMR showed compound 40 (Rf=0.80, 50% methylene chloride in hexane) as the major product. The reaction mixture was cooled to room temperature and the precipitated solids were removed by filteration and washed well with carbon tetrachloride. The filterate was washed water (2×50 mL), saturated sodium chloride solution (50 mL), dried over sodium sulfate and filtered. The filtrate was removed by rotary evaporation to yield a yellow oil. The oil was purified by column chromatography using a mixture of 40% methylene chloride in hexane as the eluant to yield compound 40 (1.92 g, 71%) as a white solid. $^1$H NMR (CDCl$_3$, 300 MHz): 7.72 (m, 2H), 7.56 (m, 2H), 7.01 (m, 4H). EI-MS: 542 (M$^+$+6, 4%), 540 (M$^+$+4, 12%), 538 (M$^+$+2, 17%), 536 (M$^+$, 11%), 462 (M$^+$+5 -Br, 3%), 461 (M$^+$+4-Br, 4%), 460 (M$^+$+3-Br, 6%), 459 (M$^+$+2-Br, 5%), 458 (M$^+$+1-Br, 6%), 457 (M$^+$-Br, 2%), 383 (M$^+$+5-2Br, 3%), 382 (M$^+$+4-2Br, 7%), 381 (M$^+$+3-2Br, 17%), 380 (M$^+$+2-2Br, 11), 379 (M$^+$+1-2Br, 6%), 378 (M$^+$-2Br, 6%), 303 (M$^+$+4-3Br, 3%), 302 (M$^+$+3-3Br, 10%), 301 (M$^+$+2-3Br, 44%), 300 (M$^+$+1-3Br, 11%), 299 (M$^+$-3Br, 44%), 222 (M$^+$+2-4Br, 5%), 221 (M$^+$+1-4Br, 12%), 220 (M$^+$—4Br, 6%). CI-MS: 542 (M$^+$+6, 24%), 541 (M$^+$+5, 14%), 540 (M$^+$+4, 35%), 539 (M$^+$+3, 10%), 538 (M$^+$+2, 24%), 537 (M$^+$+1, 4%), 536 (M$^+$, 7%), 463 (M$^+$+6-Br, 34%), 462 (M$^+$+5-Br, 23%), 461 (M$^+$+4-Br, 97%), 460 (M$^+$+3-Br, 25%), 459 (M$^+$+2-Br, 100%), 458 (M$^+$+1-Br, 11%), 457 (M$^+$-Br, 36%), 383 (M$^+$+5-2Br, 16%), 382 (M$^+$+4-2Br, 38%), 381 (M$^+$+3-2Br, 30%), 380 (M$^+$+2-2Br, 64%), 379 (M$^+$+1-2Br, 18%), 378 (M$^+$-2Br, 31%), 303 (M$^+$+4 -3Br, 11%), 302 (M$^+$+3-3Br, 28%), 301 (M$^+$+2-3Br, 98%), 300 (M$^+$+4-3Br, 29%), 299 (M$^+$-3Br, 93%), 222 (M$^+$+2-4Br, 16%), 221 (M$^+$+1-4Br, 28%), 220 (M$^+$-4Br, 14%).

Compound $A_1D_5$ was prepared by the silver nitrate hydrolysis of compound 40. A solution of silver nitrate (0.85 g, 5 mmol in 2 mL of water) was added to a solution of compound 40 (0.54 g, 1 mmol) in 10 mL of acetonitrile and the mixture was heated at reflux. A light yellow precipitate was seen immediately and refluxing was continued for one hour. After cooling to room temperature, the reaction mixture was filtered and the filtered solids were washed well with acetonitrile. The combined filtrates were removed under reduced pressure and the yellow solid thus obtained was suspended in 50 mL of methylene chloride. The solution was filtered to remove any residual silver salts and the filtrate was concentrated by rotary evaporation to yield a yellow solid. The solid was purified by column chromatography using a mixture of 40% methylene chloride in hexane as the eluant to yield compound $A_1D_5$ (0.17 g, 67%) as a yellow solid (Rf=0.41, 50% methylene chloride in hexane). $\lambda_{max}$=336 nm (acetone) $^1$H NMR (CDCl$_3$, 200 MHz): 8.16–8.09 (m, 2H), 8.06–7.99 (m, 2H), 6.93–6.91 (m, 4H). 13C NMR (CDCl$_3$, 50 MHz): 189.7, 147.1, 140.4, 137.6, 124.8, 122.6, 108.9, 77.2. EI-MS: 252 (M$^+$, 74%), 224 (M$^+$-CO, 6%), 208 (M$^+$-CO—O, 5%). CI-MS: 253 (MH$^+$, 100%), 252 (M$^+$, 39%), 225 (MH$^+$-CO, 2%).

6,11-Dioxotribenzo-spiro[4,6]undecane (41) was prepared using an approach similar to that used for the preparation of compound 39. Benzene (200 mL, spectrophotometric grade, dried over 4 A sieves for at least one day before use) was added to a mixture of 2-indanone (2.64 g, 0.02 mol), 2,2'-dihydroxybiphenyl (D$_6$, 18.6 g, 0.1 mol, Rf=0.38, 20% ethyl acetate in hexane) and p-toluenesulfonic acid (0.1 g) under an argon atmosphere. The reaction vessel was equipped with a Dean-Stark trap for azeotropic removal of water. The solution was brought to reflux and the reaction was followed by TLC, using a mixture of 20% ethyl acetate in hexane as the eluant. After refluxing overnight, the reaction mixture was cooled to room temperature and then washed with 5% sodium hydroxide solution (2×100 mL) to remove excess biphenol and residual p-toluenesulfonic acid. The benzene layer was separated and then washed with saturated sodium chloride solution (100 mL), dried over sodium sulfate, filtered and the solvent was removed under reduced pressure to yield a dark brown oil. The oil was then purified by column chromatography using a mixture of 10% ethyl acetate in hexane as the eluant to yield compound 41 (0.43 g, 7%) as a greyish white solid (Rf=0.76, 20% ethyl acetate in hexane). $^1$H NMR (CDCl$_3$, 200 MHz): 7.52 (m, 2H), 7.34 (m, 4H), 7.23 (m, 4H), 7.11 (m, 2H), 3.48 (s, 4H). EI-MS: 300 (M$^+$, 100%), 286 (M$^+$-CH$_2$, 1%), 270 (M$^+$-CH$_2$—O, 5%), 185 (MH$^+$-C$_6$H$_4$—2CH$_2$—C, 14%), 168 (M$^+$-C$_6$H$_4$—2CH$_2$—C—O, 12%), 152 (M$^+$-C$_6$H$_4$—2CH$_2$—C—2O, 2%), 115 (M$^+$-2C$_6$H$_4$—2O—H, 69%).

6,11-Dioxotribenzo-2,2-5,5-tetrabromo-spiro[4,6]undecane (42) was prepared by the benzylic bromination of compound 41 using an approach similar to that used for the preparation of compound 40.

Compound $A_1D_6$ was prepared by the silver nitrate hydrolysis of compound 42 using approach described for preparation of compound $A_1D_5$. Compound $A_1D_6$ was purified by column chromatography using a mixture of 15% ethyl acetate in hexane as the eluant to yield 57% of yellow solid (Rf=0.44, 20% ethyl acetate in hexane). $\lambda_{max}$=368 nm (CHCl$_3$) $^1$H NMR (CDCl$_3$, 200 MHz): 8.14–8.09 (m, 2H), 8.01–7.96 (m, 2H), 7.59–7.54 (m, 2H), 7.42–7.34 (m, 4H), 7.14–7.09 (m, 2H). $^{13}$C NMR (CDCl$_3$, 50 MHz): 190.8, 150.6, 139.3, 137.2, 131.4, 129.1, 128.7, 126.4, 124.7, 122.7, 77.1. EI-MS: 329 (M$^+$+1, 18%), 328 (M$^+$, 83%), 300 (M$^+$-CO, 1%), 284 (M$^+$-CO—O, 1%).

Compound u-$A_1D_7$: The reaction was carried out using 0.25 g of compound D$_7$ and an equimolar amount of compound A$_1$. The pure compound was isolated after column chromatography (Rf=0.48, 30% ethyl acetate in hexane) in 71% yield. Upon recrystallization from benzene, green needles of compound u-$A_1D_7$ were obtained. $\lambda_{max}$= 558 nm (CHCl$_3$) $^1$H NMR (acetone-d$_6$, 300 MHz): 8.37 (d, J=8 Hz, 1H), 8.04 (td, J=8 Hz, J=1 Hz, 1H), 7.87 (dd, J=8 Hz, J=1 Hz, 1H), 7.74 (td, J=8 Hz, J=1 Hz, 1H), 7.26 (m, 2H), 7.18 (m, 2H). $^{13}$C NMR (CDCl$_3$, 50 MHz): 188.0, 187.6, 144.1, 138.3, 136.9, 135.0, 131.2, 128.0, 127.3, 126.7, 124.2, 121.9. EI-MS: 284 (M$^+$, 89%), 256 (M$^+$-CO, 26%), 228 (M$^+$-2CO, 100%), 184 (M$^+$-2CO—SC, 19%).

Compound $A_1D_8$: The reaction was carried out using 0.21 g of compound D$_8$ and an equimolar amount of compound A$_1$. The pure compound was isolated in 65% yield after column chromatography (Rf=0.35, 20% ethyl acetate in hexane). Recrystallization from 20% ethyl acetate in hexane gave reddish-brown needles of compound $A_1D_8$. $\lambda_{max}$=466 nm (CH$_2$Cl$_2$) $^1$H NMR (CDCl$_3$, 300 MHz): 8.09 (m, 2H), 7.96 (m, 2H), 7.10 (dt, J=8 Hz, J=1 Hz, 1H), 6.95 (dd, J=8 Hz, J=8 Hz, J=1 Hz, 1H), 6.73 (dt, J=8 Hz, J=1 Hz, 1H), 6.45 (d, J=8 Hz, 1H), 2.78 (s, 3H). $^{13}$C NMR (CDCl$_3$, 90 MHz): 192.4, 147.5, 140.1, 136.9, 127.0, 124.6, 121.9, 121.1, 119.5, 107.4, 78.9, 31.7. EI-MS: 281 (M$^+$, 57%), 252 (M$^+$-NCH$_3$, 7%), 224 (M$^+$-NCH$_3$—CO, 100%).

Compound u-$A_1D_9$: The reaction was carried out using 0.19 g of.compound D$_9$ and an equimolar amount of compound A$_1$. The pure compound (Rf=0.74, 30% ethyl acetate in hexane) was isolated after column chromatography, using 20% ethyl acetate in hexane as the eluant, in 69% yield. $\lambda_{max}$=440 nm (acetone) $^1$H NMR (CDCl$_3$, 300 MHz): 8.08 (dd, J=8 Hz, J=1 Hz, 1H), 7.96–7.82 (m, 4H), 7.69 (td, J=8 Hz, J=1 Hz, 1H), 7.54 (dd, J=8 Hz, J=1 Hz, 2H), 7.46 (t, J=8 Hz, 2H). $^{13}$C NMR (CDCl$_3$, 75 MHz): 187.0, 183.9, 146.2, 138.3, 135.2, 134.1, 132.4, 131.2, 129.3, 128.6, 127.6, 126.5, 125.6, 125.1, 124.4. EI-MS: 334 (M$^+$, 37%), 306 (M$^+$-CO, 29%), 278 (M$^+$-2CO, 27%), 277 (M$^+$-2CO—H, 100%), 246 (m$^+$-2CO—S, 31%).

Compound u-$A_1D_{10}$: The reaction was carried out using 0.050 g of compound D$_{10}$ and an equimolar amount of compound $A_1$. The pure compound (Rf=0.54, 40% ethyl acetate in hexane) was isolated after column chromatography, using 30% ethyl acetate in hexane as the eluant, in 61% yield. $\lambda_{max}$=424 nm (CH$_2$Cl$_2$) $^1$H NMR (CDCl$_3$, 200 MHz): 8.08–7.92 (m, 3H), 7.84–7.63 (m, 3H), 7.56–7.38 (m, 2H), 7.32 (dd, J=7 Hz, J=1 Hz, 1H), 7.21 (dd, J=8 Hz, J=1 Hz, 1H). $^{13}$C NMR (CDCl$_3$, 50 MHz): 187.1, 183.8, 150.2, 145.9, 138.2, 136.8, 135.2, 133.9, 131.6, 127.9, 127.0, 126.9, 125.7, 124.3, 124.2, 123.8, 123.6, 118.6, 113.8. EI-MS: 318 (M$^+$, 54%), 290 (M$^+$-CO, 60%), 262 (M$^+$-2CO, 100%), 246 (M$^+$-2CO—O, 11%), 230 (M$^+$-2CO—S, 12%). CI-MS: 319 (MH$^+$, 100%), 318 (M$^+$, 21%), 290 (M$^+$-CO, 19%), 262 (M$^+$-2CO, 10%).

Compound $A_1D_{11}$: The reaction was carried out using 0.47 g of compound $D_{11}$ and an equimolar amount of compound $A_1$. The pure compound (Rf=0.72, 40% ethyl acetate in hexane) was isolated after column chromatography, using 20% ethyl acetate in hexane as the eluant, in 53% yield. Upon recrystallization from 20% ethyl acetate in hexane, orange needles of compound $A_1D_{11}$ were obtained. $\lambda_{max}$=370 nm (CH$_2$Cl$_2$) $^1$H NMR (CDCl$_3$, 300 MHz): 8.01–7.98 (m, 2H), 7.92–7.89 (m, 2H), 7.72 (dd, J=8 Hz, J=1 Hz, 1H), 7.51 (t, J=8 Hz, 1H), 7.44 (dd, J=8 Hz, J=1 Hz, 1H), 7.35 (t, J=8 Hz, 1H), 7.19 (dd, J=7 Hz, J=1 Hz, 1H), 7.01 (dd, J=8 Hz, J=1 Hz, 1H), 3.09 (s, 3H). $^{13}$C NMR (CDCl$_3$, 50 MHz): 192.4, 142.5, 138.7, 136.6, 133.9, 127.9, 127.1, 125.2, 124.4, 123.8, 123.5, 120.6, 120.3, 110.6, 68.1, 37.1. EI-MS: 331 (M$^+$, 100%), 316 (M$^+$-CH$_3$, 6%), 302 (M$^+$-NCH$_3$, 6%), 274 (M$^+$-NCH$_3$—CO, 92%), 271 (M$^+$-CO—S, 7%), 256 (M$^+$-CO—S —CH$_3$, 3%).

Compound u-$A_1D_{11}$: The reaction was carried out using 0.47 g of compound $D_{11}$ and an equimolar amount of compound $A_1$. The pure compound (Rf=0.65, 40% ethyl acetate in hexane) was isolated after column chromatography, using 20% ethyl acetate in hexane as the eluant, in 21% yield. Upon recrystallization from 20% ethyl acetate in hexane, black needles of compound u-$A_1D_{11}$ were obtained. $\lambda_{max}$=470 and 588 nm (CHCl$_3$) $^1$H NMR (CDCl$_3$, 200 MHz): 8.01 (d, J=7 Hz, 1H), 7.96–7.88 (m, 2H), 7.78–7.65 (m, 2H), 7.58–7.46 (m, 2H), 7.37 (dd, J=8 Hz, J=7 Hz, 1H), 7.19 (dd, J=7 Hz, J=1 Hz, 1H), 7.05 (dd, J=7 Hz, J=2 Hz, 1H), 2.99 (s, 3H). $^{13}$C NMR (CDCl$_3$, 50 MHz): 191.2, 184.4, 147.1, 142.5, 138.1, 135.8, 134.0, 130.8, 128.3, 127.3, 127.1, 125.4, 125.1, 124.8, 122.4, 120.4, 119.2, 110.0, 104.4, 36.6. EI-MS: 331 (M$^+$, 5%), 303 (M$^+$-CO, 28%), 288 (M$^+$-CO—CH$_3$, 19%), 275 (M$^+$-2CO, 25%), 274 (M$^+$-NCH$_3$—CO, 100%), 271 (M$^+$-CO—S, 4%), 260 (M$^+$-2CO—CH$_3$, 3%), 256 (M$^+$-CO—S—CH$_3$, 2%), 246 (M$^+$-2CO—NCH$_3$, 5%), 243 (M$^+$-2CO—S, 3%), 228 (M$^+$-2CO—S —CH$_3$, 4%).

Compound $A_2D_9$: The reaction was carried out using 0.19 g of compound $D_9$ and an equimolar amount of compound $A_2$. The pure compound (Rf=0.73, 30% ethyl acetate in hexane) was isolated after column chromatography, using 15% ethyl acetate in hexane as the eluant, in 12% yield. $\lambda_{max}$=374 nm (CH$_2$Cl$_2$) $^1$H NMR (CDCl$_3$, 200 MHz): 8.04 (s, 2H), 7.83 (dd, J=8 Hz, J=1 Hz, 2H), 7.53 (dd, J=7 Hz, J=2 Hz, 2H), 7.45 (dd, J=8 Hz, J=7 Hz, 2H). $^{13}$C NMR (CDCl$_3$, 50 MHz): 188.3, 142.2, 137.7, 134.0, 129.3, 127.4, 126.3, 126.2, 125.8. EI-MS: 406 (M$^+$+4, 17%), 405 (M$^+$+3, 15%), 404 (M$^+$+2, 73%), 403 (M$^+$1, 22% ), 402 (M$^+$, 99%), 372 (M$^+$+2-S, 2%), 370 (M$^+$-S, 3%), 346 (M$^+$+4-S—CO, 20%), 345 (M$^+$+3-S—CO, 100%), 344 (M$^+$+2-S—CO, 3%), 311 (M$^+$2-S—Cl—2H —CO, 10%), 310 (M$^+$+1-S—Cl—2H—CO, 3%).

Compound u-$A_2D_9$: The reaction was carried out using 0.19 g of compound $D_9$ and an equimolar amount of compound $A_2$. The pure compound (Rf=0.58, 30% ethyl acetate in hexane) was isolated after column chromatography, using 15% ethyl acetate in hexane as the eluant, in 47% yield. $\lambda_{max}$430 nm (acetone) $^1$H NMR (CDCl$_3$, 200 MHz): 8.05 (s, 1H), 7.95 (s, 1H), 7.84 (dd, J=8 Hz, J=2 Hz, 2H), 7.52 (dd, J=7 Hz, J=2 Hz, 2H), 7.45 (dd, J=8 Hz, J=7 Hz, 2H). $^{13}$C NMR (CDCl$_3$, 50 MHz): 185.3, 182.0, 146.7, 145.0, 143.3, 136.8, 134.1, 131.5, 129.8, 129.6, 127.9, 126.8, 126.7, 125.7, 124.2. EI-MS: 406 (M$^+$+4, 6%), 405 (M$^+$+3, 7%), 404 (M$^+$+2, 21%), 403 (M$^+$+1, 7%), 402 (M$^+$, 27%), 378 (M$^+$+4-CO, 6%), 377 (M$^+$+3-CO, 5%), 376 (M$^+$+2-CO, 16%), 375 (M$^+$+1-CO, 6%) 374 (M$^+$-CO, 19%), 372 (M$^+$+2-S, 2%), 370 (M$^+$-S, 3%), 350 (M$^+$+4-2CO, 350(M$^+$+4 —2CO, 12%), 349(M$^+$+3-2CO, 29%), 348 (M$^+$+2-2CO, 31%), 347 (M$^+$+1-2CO, 84%), 346 (M$^+$-2CO, 40%), 345 (M$^+$+3-S—CO, 100%), 344 (M$^+$+2-S—CO, 18%), 343 (M$^+$+1-S—CO, 4%), 342 (M$^+$+2-S—CO, 3%), 318 (M$^+$+4-S—2CO, 4%), 317 (M$^+$+3-S—2CO, 10%), 315 (M$^+$+1-S—2CO, 8%), 314 (M$^+$-S—2CO, 16%), 283 (M$^+$+4-S—Cl—2CO, 4%), 282 (M$^+$+3-S—Cl—2CO, 8%), 281 (M$^+$+2-S—Cl—2CO, 19%), 280 (M$^+$+1-S—Cl—2CO, 10%), 279 (M$^+$-S—Cl—2CO, 46%).

Compound $A_8D_{11}$: The reaction was carried out using 0.43 g of compound $D_{11}$ and an equimolar amount of compound $A_8$. The pure compound (Rf=0.45, 30% ethyl acetate in hexane) was isolated after column chromatography, using 20% ethyl acetate in hexane as the eluant, in 34% yield. Upon recrystallization from 20% ethyl acetate in hexane, orange needles of compound $A_8D_{11}$ were obtained. $\lambda_{max}$=370 nm (CH$_2$Cl$_2$) $^1$H NMR (CDCl$_3$, 300 MHz): 7.92 (d, J=8 Hz, 1H), 7.70 (dd, J=8 Hz, J=1 Hz, 1H), 7.51–7.30 (m, 5H), 7.19 (dd, J=7 Hz, J=1 Hz, 1H), 698 (dd, J=8 Hz, J=1 Hz, 1H), 3.95 (s, 3H), 3.07 (s, 3H). $^{13}$C NMR (CDCl$_3$, 50 MHz): 192.5, 191.1, 166.8, 142.5, 141.6, 133.9, 132.0, 127.7, 127.0, 126.2, 125.2, 125.1, 124.0, 123.3, 120.5, 120.2, 110.3, 105.8, 68.3, 56.3, 36.9. EI-MS: 361 (M$^+$, 100%), 346 (M$^+$CH$_3$, 8%), 332 (M$^+$-NCH$_3$, 5%), 318 (M$^+$-CH$_3$—CO, 9%), 304 (M$^+$-NCH$_3$—CO, 63%).

Compound u-$A_8$-m-$D_{11}$: The reaction was carried out using 0.43 g of compound $D_{11}$ and an equimolar amount of compound $A_8$. The pure compound (Rf= 0.34, 30% ethyl acetate in hexane) was isolated after column chromatography, using 20% ethyl acetate in hexane as the eluant, in 16% yield. $\lambda_{max}$=450 and 564 nm (CH$_2$Cl$_2$) $^1$H NMR (CDCl$_3$, 200 MHz): 7.96 (d, J=8 Hz, 1H), 7.74 (dd, J=8 Hz, J=1 Hz, 1H), 7.52–7.28 (m, 4H), 7.21–7.14 (m, 2H), 7.03 (dd, J=8 Hz), J=2 Hz, 1H), 3.99 (s, 3H), 2.97 (s, 3H). $^{13}$C NMR (CDCl$_3$, 50 MHz): 192.2, 182.0, 167.6, 150.5, 142.5, 134.0, 130.1, 128.1, 127.3, 127.0, 125.2, 125.1, 122.4, 120.4, 119.9, 119.1, 109.9, 109.8, 62.6, 56.3, 36.5. EI-MS: 361 (M$^+$, 16%), 333 (M$^+$-CO, 61%), 318 (M$^+$-CO—CH$_3$, 60%), 305 (M$^+$-2CO, 22%), 304 (M$^+$-NCH$_{3-CO}$, 100%), 301 (M$^+$-CO—S, 4%), 290 (M$^+$-2CO—CH$_3$, 8%), 286 (M$^+$-CO—S—CH$_3$, 2%), 276 (M$^+$-2CO—NCH$_3$, 2%), 273 (M$^+$-2CO—S, 4%), 258 (M$^+$-2CO—S—CH$_3$, 2%).

Compound u-$A_8$-p-$D_{11}$: The reaction was carried out using 0.34 g of compound $D_{11}$ and an equimolar amount of compound $A_8$. The pure compound (Rf=0.37, 30% ethyl acetate in hexane) was isolated after column chromatography, using 20% ethyl acetate in hexane as the eluant, in 4% yield. $\lambda_{max}$=472 and 592 nm (CH$_2$Cl$_2$) $^1$H NMR (CDCl$_3$, 200 MHz): 7.79 (d, J=8 Hz, 1H), 7.74 (dd, J=8 Hz, J=1 Hz, 1H), 7.53–7.32 (m, 5H), 7.18 (dd, J=7 Hz, J=1 Hz, 1H), 702 (dd, J=8 Hz, J=2 Hz, 1H), 3.95 (s, 3H), 2.97 (s, 3H). $^{13}$C NMR (CDCl$_3$, 50 MHz): 191.3, 184.3, 161.5, 142.5, 140.0, 137.4, 134.0, 131.2, 128.6, 128.1, 127.6, 127.0, 125.8, 125.1, 122.2, 120.4, 110.0, 105.8, 62.3, 56.0, 36.3. EI-MS:

361 (M$^+$, 6%), 333 (M$^+$-CO, 27%), 318 (M$^+$-CO—CH$_3$, 21%), 305 (M$^+$-2CO, 23%), 304 (M$^+$-NCH$_3$—CO, 100%), 301 (M$^+$-CO—S, 2%), 290 (M$^+$-2CO—CH$_3$, 3%), 286 (M$^+$-CO—S—CH$_3$, 1%), 276 (M$^+$-2CO—NCH$_3$, 2%), 273 (M$^+$-2CO—S, 3%), 258 (M$^+$-2CO—S—CH$_3$, 1%).

Compound A$_9$D$_{11}$: The reaction was carried out using 0.20 g of compound D$_{11}$ and an equimolar amount of compound A$_9$. The pure compound (Rf=0.39, 30% ethyl acetate in hexane) was isolated after column chromatography, using 20% ethyl acetate in hexane as the eluant, in 57% yield. $\lambda_{max}$=355 nm (CH$_2$Cl$_2$) $^1$H NMR (CDCl$_3$, 300 MHz): 7.97–7.90 (m, 3H), 7.77–7.71 (m, 2H), 7.63–7.43 (m, 6H), 7.36 (t, J=7 Hz, 1H), 7.20 (dd, J=7 Hz, J=1 Hz, 1H), 7.02 (dd, J=7 Hz, J=1 Hz, 1H), 3.07 (s, 3H). $^{13}$C NMR (CDCl$_3$, 50 MHz): EI-MS: 487 (M$^+$, 95%), 472 (M$^+$-CH$_3$, 4%), 458 (M$^+$-NCH$_3$, 3%), 444 (M$^+$-CH$_3$—CO, 2%), 430 (M$^+$-NCH$_3$—CO, 7%), 346 (M$^+$-C$_6$H$_5$SO$_2$, 100%), 318 (M$^+$-C$_6$H$_5$SO$_2$—CO, 100%), 303 (M$^+$-C$_6$H$_5$SO$_2$—CO—CH$_3$, 6%), 289 (M$^+$-C$_6$H$_5$SO$_2$—CO—NCH$_3$, 8%).

Compound A$_{10}$D$_{11}$: The reaction was carried out using 0.02 g of compound D$_{11}$ and an equimolar amount of compound A$_{10}$. The pure compound (Rf=0.31, 30% ethyl acetate in hexane) was isolated after column chromatography, using 20% ethyl acetate in hexane as the eluant, in 42% yield. $\lambda_{max}$=363 nm (CH$_2$Cl$_2$) $^1$H NMR (CDCl$_3$, 200 MHz): 8.05 (d, J=8 Hz, 1H), 7.87–7.79 (m, 2H), 7.73 (dd, J=8 Hz, J=1 Hz, 1H), 7.51–7.32 (m, 3H), 7.21 (dd, J=7 Hz, J=1 Hz, 1H), 7.02 (dd, J=8 Hz, J=1 Hz, 1H), 3.90 (d, J=15 Hz, 1H), 3.31 (d, J=15 Hz, 1H), 3.10 (s, 3H), 2.62–2.37 (m, 2H), 2.24–2.01 (m, 3H), 1.87–1.72 (m, 1H), 1.56–1.43 (m, 1H), 1.16 (s, 3H), 0.93 (s, 3H). $^{13}$C NMR (CDCl$_3$, 50 MHz): EI-MS: 561 (M$^+$, 100%), 532 (M$^+$-NCH$_3$, 4%), 504 (M$^+$-NCH$_3$—CO, 5%), 346 (M$^+$-camphorsulfonyl, 100%), 331 (M$^+$-camphorsulfonyl-CH$_3$, 9%), 318 (M$^+$-camphorsulfonyl-CO, 8%), 303 (M$^+$-camphorsulfonyl-CO—CH$_3$, 4%), 289 (M$^+$-camphorsulfonyl-CO—NCH$_3$, 4%).

Compound A$_8$D$_{12}$: The reaction was carried out using 0.04 g of compound D$_{12}$ and an equimolar amount of compound A$_8$. The pure compound (Rf=0.72, 20% ethyl acetate in hexane) was isolated after column chromatography, using 10% ethyl acetate in hexane as the eluant, in 9% yield. $\lambda_{max}$=362 nm (CH$_2$Cl$_2$) $^1$H NMR (CDCl$_3$, 300 MHz): 7.93 (d, J=8 Hz, 1H), 7.68 (m, 2H), 7.320 (m, 5H), 7.08 (dd, J=8 Hz, J=1 Hz, 1H), 4.25 (sextet, J=7 Hz, 1H), 3.96 (s, 3H), 1.68–1.42 (m,2 H), 1.25 (d, J=7 Hz, 3H), 086 (t, J=7 Hz, 3H). $^{13}$C NMR (CDCl$_{13}$, 50 MHz): CI-MS: 404 (MH$^+$, 76%), 403 (M$^+$, 100%), 388 (M$^+$-CH$_3$, 3%), 374 (MH$^+$-CO, 5%), 347 (MH$^+$-C$_4$H$_9$, 19%), 346 (M$^+$-C$_4$H$_9$, 12%), 318 (M$^+$-C$_4$H$_9$—CO, 8%).

Thus, preferred embodiments of the invention are illustrated and described in this disclosure. It is understood that this invention is capable of variation and modification. Therefore, it is not wished or intended to be limited to the precise terms set forth, but rather it is desired and intended to include such changes and alterations which may be made for adopting the invention of the present invention to various usuages and conditions. Accordingly, such changes and alterations are properly intended to be within the full range of equivalents and, therefore, within the purview of the following claims. The terms and expressions which have been employed in the foregoing specification are used therein as terms of description and not of limitation. Thus there is no intention in the use of such terms and expressions to exclude equivalents of features shown and described or portions thereof, it being recognized that the scope of the invention is defined and limited only by the claims which follow.

Thus is described my invention and the manner and processing of making and using it in such full, clear, concise, and exact terms so as to enable any person skilled in the art to which it pertains, or with which it is most nearly connected, to make and use the same.

What is claimed is:

1. A compound having the formula

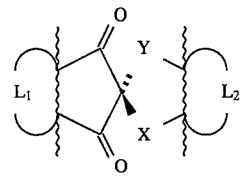

wherein X and Y are nitrogen substituted by an alkyl or aryl group R substituent selected from the group consisting of methyl, ethyl, propyl, isobutyl, benzyl and phenyl;

and the linkers L$_1$, L$_2$ have the formula

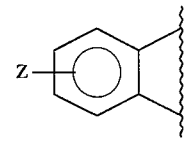

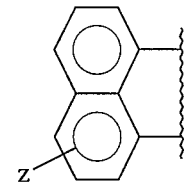

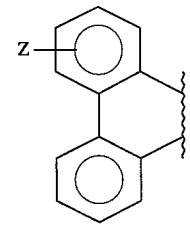

or

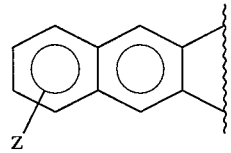

wherein Z is optionally present and is one or more substituents on any available carbon, said one or more Z substituents being selected from the group consisting of halogens, nitro-, amino-, dimethylamino-, trimethylammonium-, hydroxy-, alkoxy-, thiomethyl-, sulfoxy-, sulfonyl- and cyano-.

2. The compound according to claim 1 having one of the following formulas:

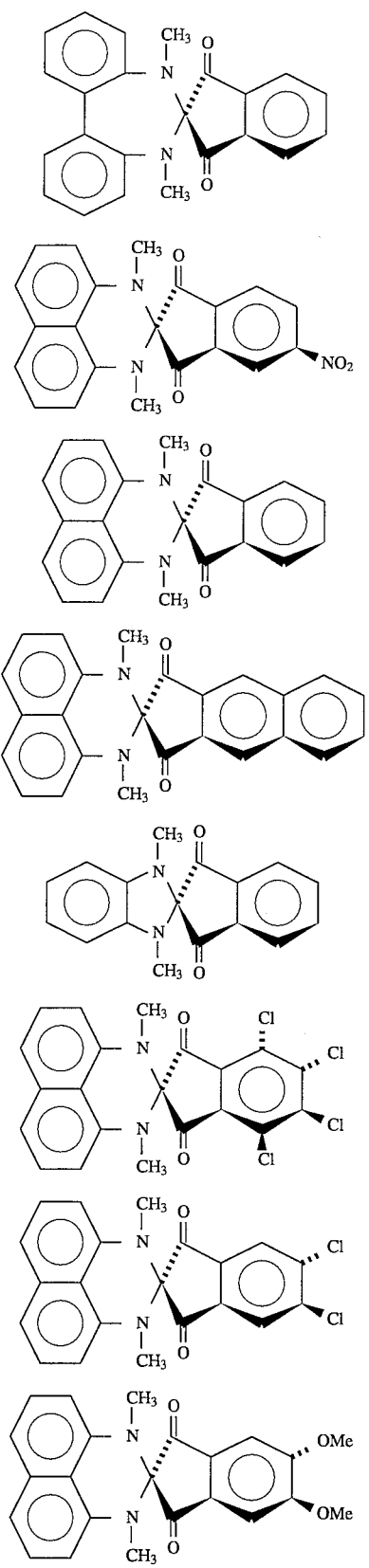

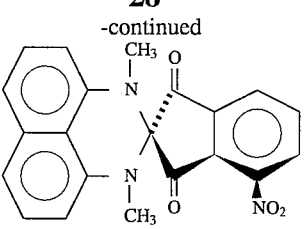

3. A compound having the formula

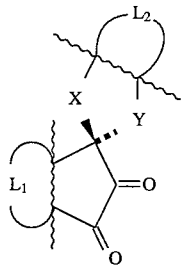

wherein X and Y are nitrogen substituted by an alkyl or an aryl group R substituent selected from the group consisting of methyl, ethyl, propyl, isobutyl, benzyl and phenyl;

and the linkers $L_1$, $L_2$ have the formula

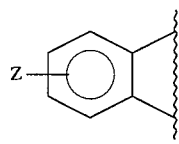

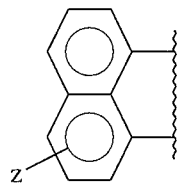

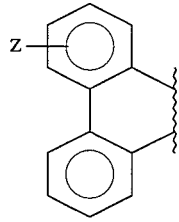

or

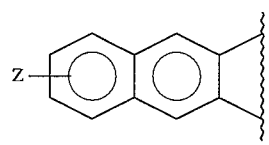

wherein Z is optionally present and is one or more substituents on any available carbon, said one or more Z substituents being selected from the group consisting of halogens, nitro-, amino-, dimethylamino-, trimethylammonium-, hydroxy-, alkoxy-, thiomethyl-, sulfoxy-, sulfonyl- and cyano-.
4. The compound according to claim 3 having one of the following formulas:
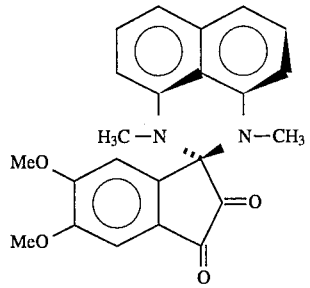
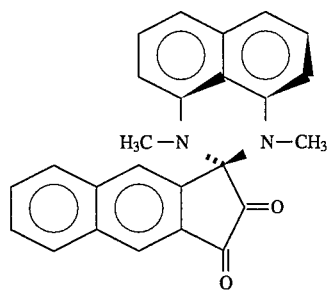
* * * * *